(12) United States Patent
Czaplewski

(10) Patent No.: US 12,161,580 B2
(45) Date of Patent: Dec. 10, 2024

(54) SOFT CONVEX OSTOMY APPLIANCE

(71) Applicant: Hollister Incorporated, Libertyville, IL (US)

(72) Inventor: Gregory J. Czaplewski, Glendale Heights, IL (US)

(73) Assignee: HOLLISTER INCORPORATED, Liberty, IL (US)

( * ) Notice: Subject to any disclaimer, the term of this patent is extended or adjusted under 35 U.S.C. 154(b) by 343 days.

(21) Appl. No.: 17/767,363

(22) PCT Filed: Dec. 3, 2020

(86) PCT No.: PCT/US2020/062997
§ 371 (c)(1),
(2) Date: Apr. 7, 2022

(87) PCT Pub. No.: WO2021/113435
PCT Pub. Date: Jun. 10, 2021

(65) Prior Publication Data
US 2022/0370232 A1  Nov. 24, 2022

Related U.S. Application Data

(60) Provisional application No. 62/945,067, filed on Dec. 6, 2019.

(51) Int. Cl.
*A61F 5/443* (2006.01)
*A61F 5/44* (2006.01)
(Continued)

(52) U.S. Cl.
CPC ...... *A61F 5/443* (2013.01); *A61F 2005/4483* (2013.01)

(58) Field of Classification Search
CPC .............. A61F 5/443; A61F 2005/4483; A61F 5/445
See application file for complete search history.

(56) References Cited

U.S. PATENT DOCUMENTS 4,419,100 A * 12/1983 Alexander ............. A61F 5/448
604/339
4,834,731 A * 5/1989 Nowak ................... A61F 5/448
604/339
(Continued)

FOREIGN PATENT DOCUMENTS

EP          0317326 A2 *  5/1989  ............. A61F 5/448
WO       02094333 A2    11/2002
WO     2018093815 A2     5/2018

OTHER PUBLICATIONS

International Preliminary Report on Patentability issued by ISA/EPO in connection with PCT/US2020/062997 on May 17, 2022.
(Continued)

*Primary Examiner* — Guy K Townsend
(74) *Attorney, Agent, or Firm* — Klintworth & Rozenblat IP LLP

(57) ABSTRACT

A convex ostomy appliance (10) may be configured to have a softness of about 32.6 N*mm to about 68.9 N*mm, wherein the softness is measured in energy expended to compress 3 mm of the convex portion, and a flexibility of about 105.2 N*mm to about 186.6 N*mm, wherein the flexibility is measured in energy expended to deform the ostomy appliance by 30%. The convex ostomy appliance may include a coupling flange (22), a floating flange film (24) having one end secured to the coupling flange, a soft convex insert (26) having a recess (46) in which another end of the floating flange film is secured, an adhesive (28) extending over the soft convex insert, and a stoma opening (18) extending through at least the coupling flange, the floating flange film and the soft convex insert.

19 Claims, 31 Drawing Sheets

(51) Int. Cl.
*A61F 5/445* (2006.01)
*A61F 5/448* (2006.01)

(56) References Cited

U.S. PATENT DOCUMENTS

| | | | | |
|---|---|---|---|---|
| 4,973,323 A * | 11/1990 | Kaczmarek | A61F 5/448 | 604/277 |
| 5,013,307 A * | 5/1991 | Broida | A61F 13/45 | 604/338 |
| 5,316,607 A * | 5/1994 | Johnsen | A61F 5/445 | 156/286 |
| 5,501,678 A * | 3/1996 | Olsen | A61F 5/443 | 604/344 |
| 5,607,413 A * | 3/1997 | Holmberg | A61F 5/448 | 604/338 |
| 5,730,735 A * | 3/1998 | Holmberg | A61F 5/448 | 604/338 |
| 6,210,384 B1 * | 4/2001 | Cline | A61F 5/448 | 604/338 |
| 6,569,134 B1 * | 5/2003 | Leise, Jr. | A61F 5/448 | 604/336 |
| 6,589,222 B1 * | 7/2003 | Olsen | A61F 5/449 | 604/336 |
| 6,673,056 B2 * | 1/2004 | Metz | A61F 5/448 | 604/338 |
| 6,740,067 B2 * | 5/2004 | Leise, Jr | A61F 5/448 | 604/336 |
| 7,029,464 B2 * | 4/2006 | Fenton | A61F 5/448 | 604/277 |
| 7,347,844 B2 * | 3/2008 | Cline | A61F 5/448 | 604/338 |
| 7,857,796 B2 * | 12/2010 | Cline | A61F 5/445 | 604/277 |
| 8,684,983 B2 * | 4/2014 | Andersen | A61F 5/445 | 604/338 |
| 9,498,371 B2 * | 11/2016 | Salama | A61F 5/445 | |
| 9,943,436 B2 * | 4/2018 | Nguyen-Demary | A61F 5/445 | |
| 9,999,537 B2 * | 6/2018 | Ekfeldt | A61F 5/445 | |
| 10,335,309 B2 * | 7/2019 | Becker | A61F 5/445 | |
| 10,786,652 B2 * | 9/2020 | Doshi | A61F 5/448 | |
| 11,051,969 B2 * | 7/2021 | Nyberg | A61F 5/443 | |
| 11,246,739 B2 * | 2/2022 | Ekfeldt | A61F 5/443 | |
| 11,484,432 B2 * | 11/2022 | Hansen | A61F 5/4404 | |
| 11,571,325 B2 * | 2/2023 | Kavanagh | A61F 5/448 | |
| 11,590,017 B2 * | 2/2023 | Donovan | A61F 5/443 | |
| 11,638,658 B2 * | 5/2023 | Donovan | A61F 5/448 | 604/344 |
| 11,679,020 B2 * | 6/2023 | Donovan | A61F 5/443 | 604/336 |
| 11,918,508 B1 * | 3/2024 | Wines | A61F 5/445 | |
| 2004/0006320 A1 * | 1/2004 | Buglino | A61F 5/448 | 604/344 |
| 2004/0106908 A1 * | 6/2004 | Leise, Jr. | A61F 5/448 | 604/355 |
| 2004/0193122 A1 * | 9/2004 | Cline | A61F 5/445 | 604/332 |
| 2004/0193123 A1 * | 9/2004 | Fenton | A61F 5/448 | 604/344 |
| 2008/0119804 A1 * | 5/2008 | Cline | A61F 5/448 | 604/338 |
| 2010/0324511 A1 * | 12/2010 | Dove | A61F 5/445 | 604/338 |
| 2011/0218507 A1 * | 9/2011 | Andersen | A61F 5/445 | 604/338 |
| 2012/0232506 A1 * | 9/2012 | Todd | A61F 5/445 | 604/339 |
| 2014/0316360 A1 * | 10/2014 | Ekfeldt | A61F 5/445 | 604/338 |
| 2015/0359656 A1 * | 12/2015 | Hansen | A61F 5/443 | 604/344 |
| 2018/0235801 A1 * | 8/2018 | Oellgaard | A61F 5/443 | |
| 2018/0325718 A1 * | 11/2018 | Ekfeldt | A61F 5/445 | |
| 2019/0231580 A1 * | 8/2019 | Czaplewski | A61F 5/448 | |
| 2020/0015996 A1 * | 1/2020 | Schertiger | A61F 5/445 | |
| 2020/0100931 A1 * | 4/2020 | Schoess | A61F 5/445 | |
| 2020/0253777 A1 * | 8/2020 | Jones | A61F 5/443 | |
| 2020/0337879 A1 * | 10/2020 | Donovan | A61F 5/443 | |
| 2020/0337884 A1 * | 10/2020 | Donovan | A61F 5/448 | |
| 2020/0337885 A1 * | 10/2020 | Donovan | A61F 5/443 | |
| 2022/0370232 A1 * | 11/2022 | Czaplewski | A61F 5/443 | |
| 2023/0201024 A1 * | 6/2023 | Donovan | A61F 5/448 | 604/344 |
| 2023/0263652 A1 * | 8/2023 | Donovan | A61F 5/443 | 604/336 |

OTHER PUBLICATIONS

International Search Report issued by ISA/EPO in connection with PCT/US2020/062997 on May 3, 2021.
Written Opinion issued by ISA/EPO in connection with PCT/US2020/062997 on May 3, 2021.

* cited by examiner

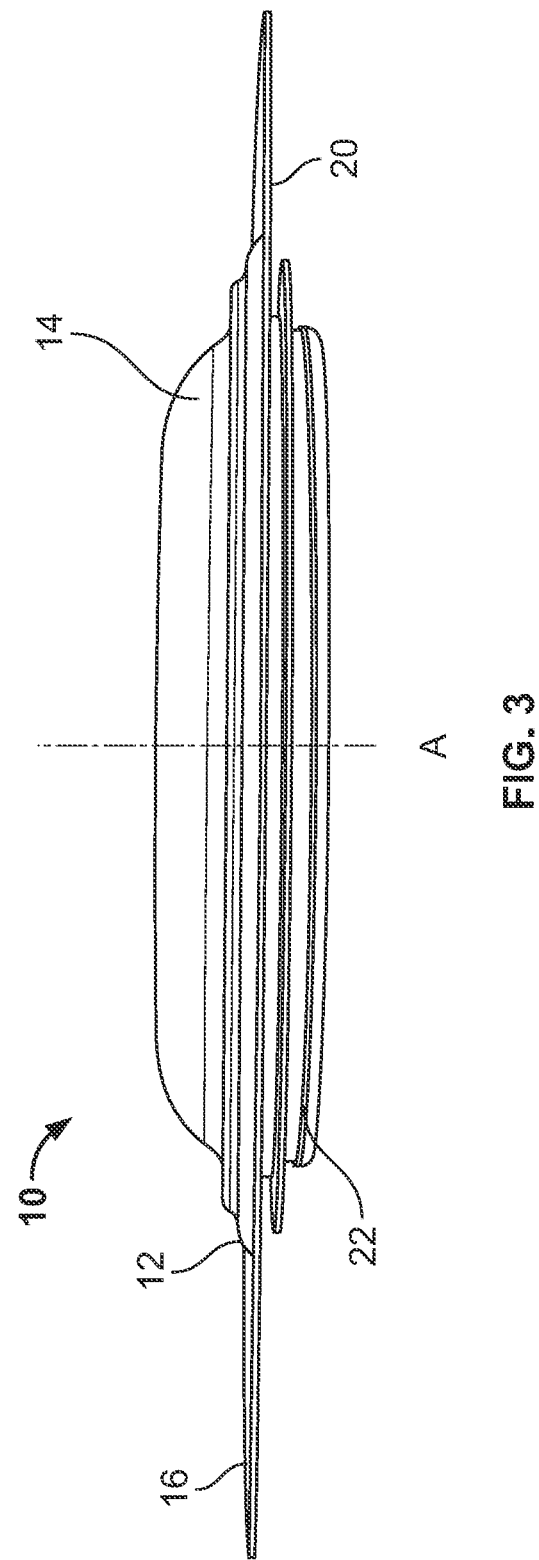

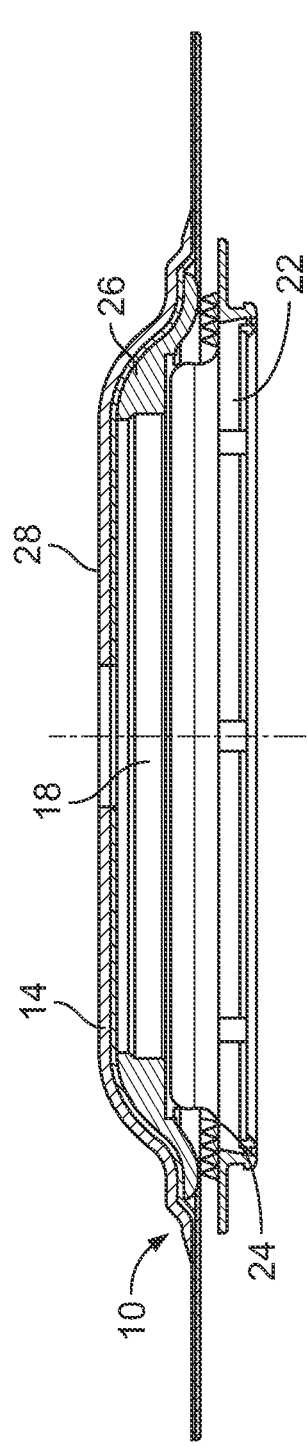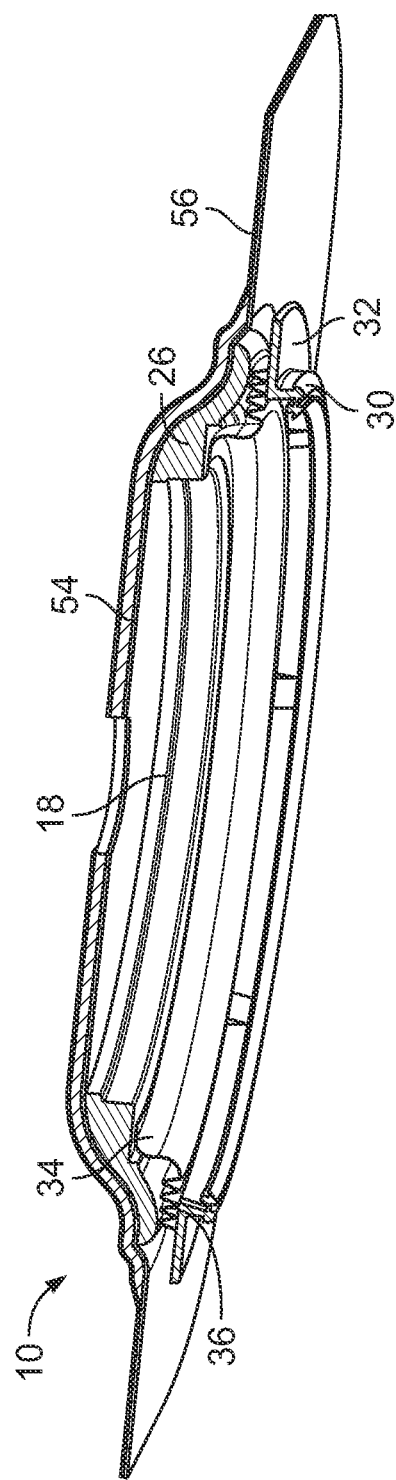

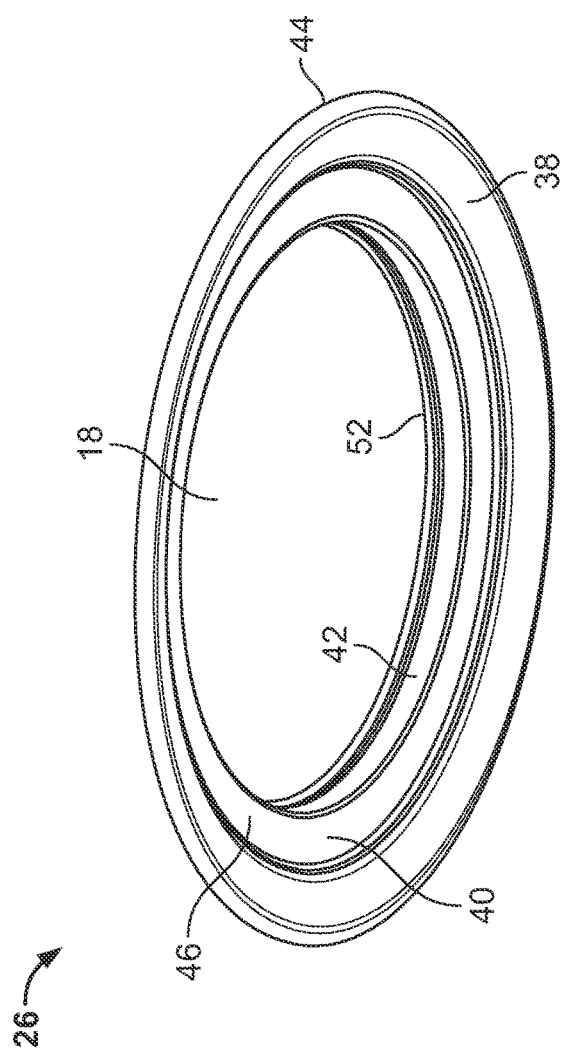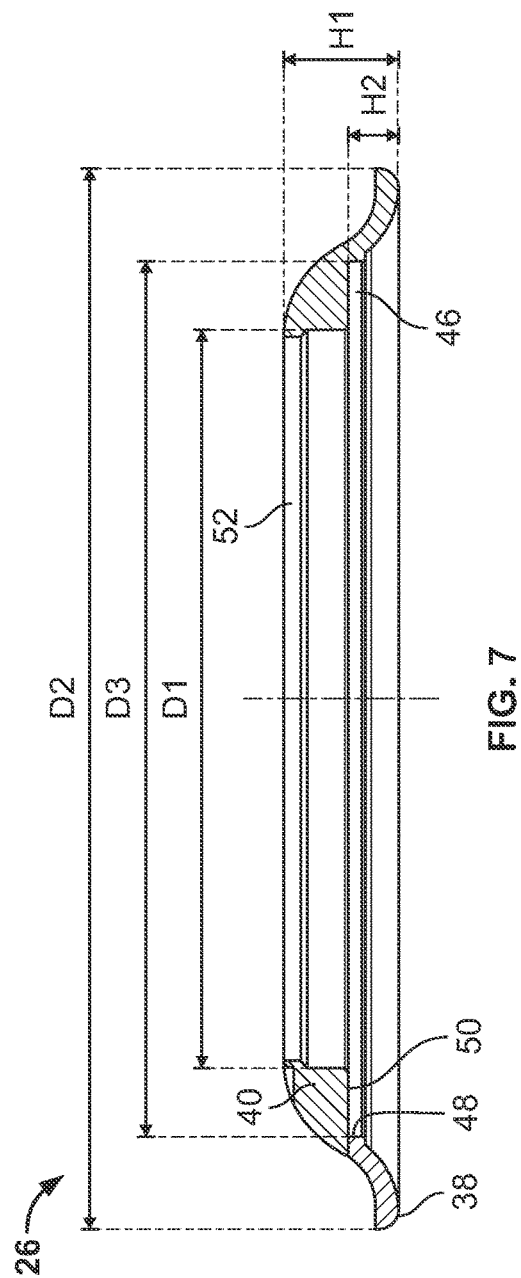
FIG. 6
FIG. 7

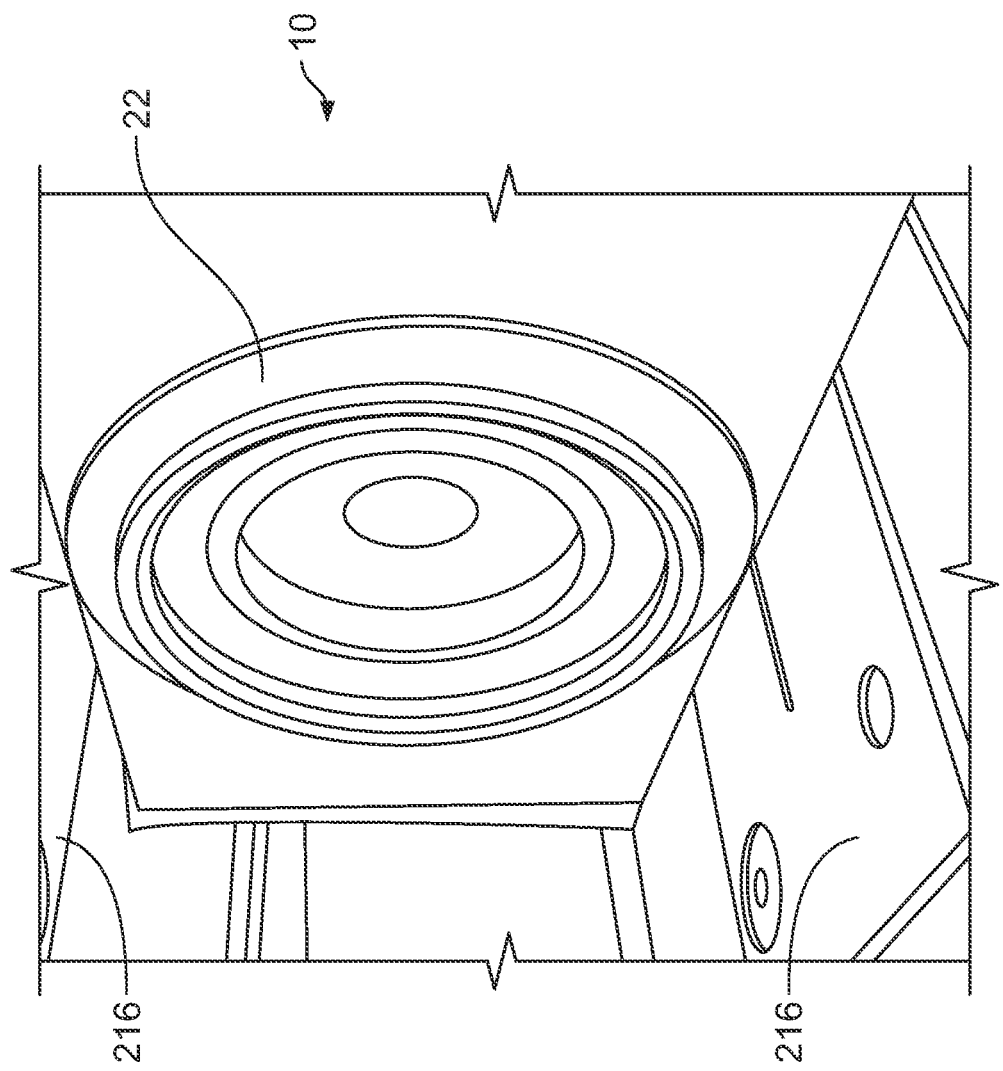

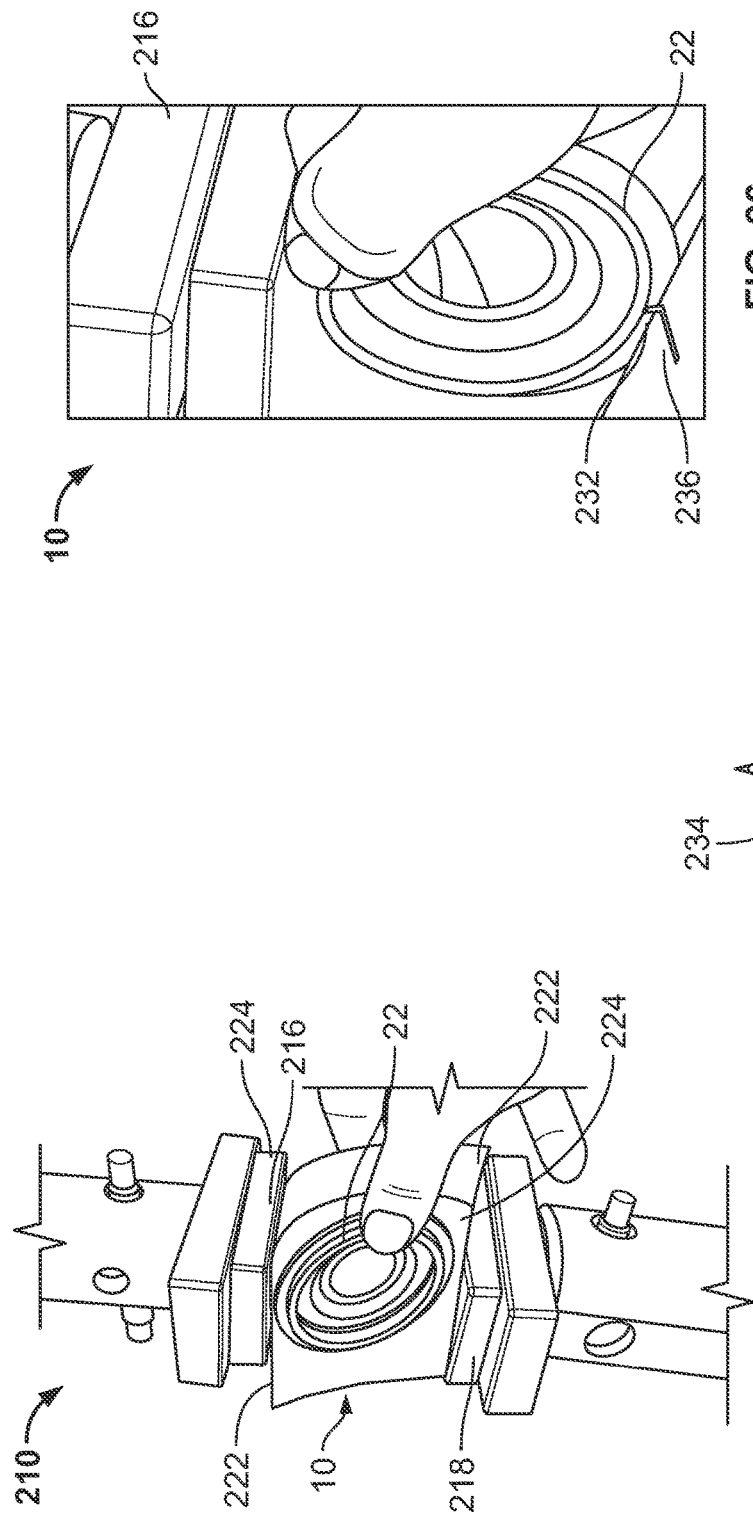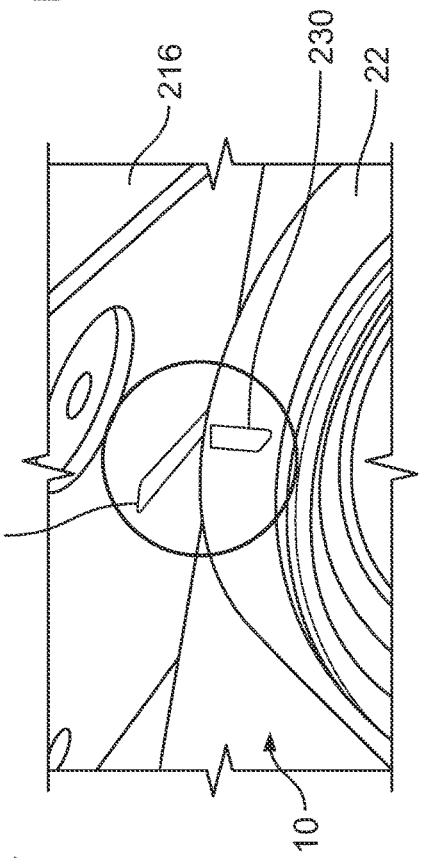

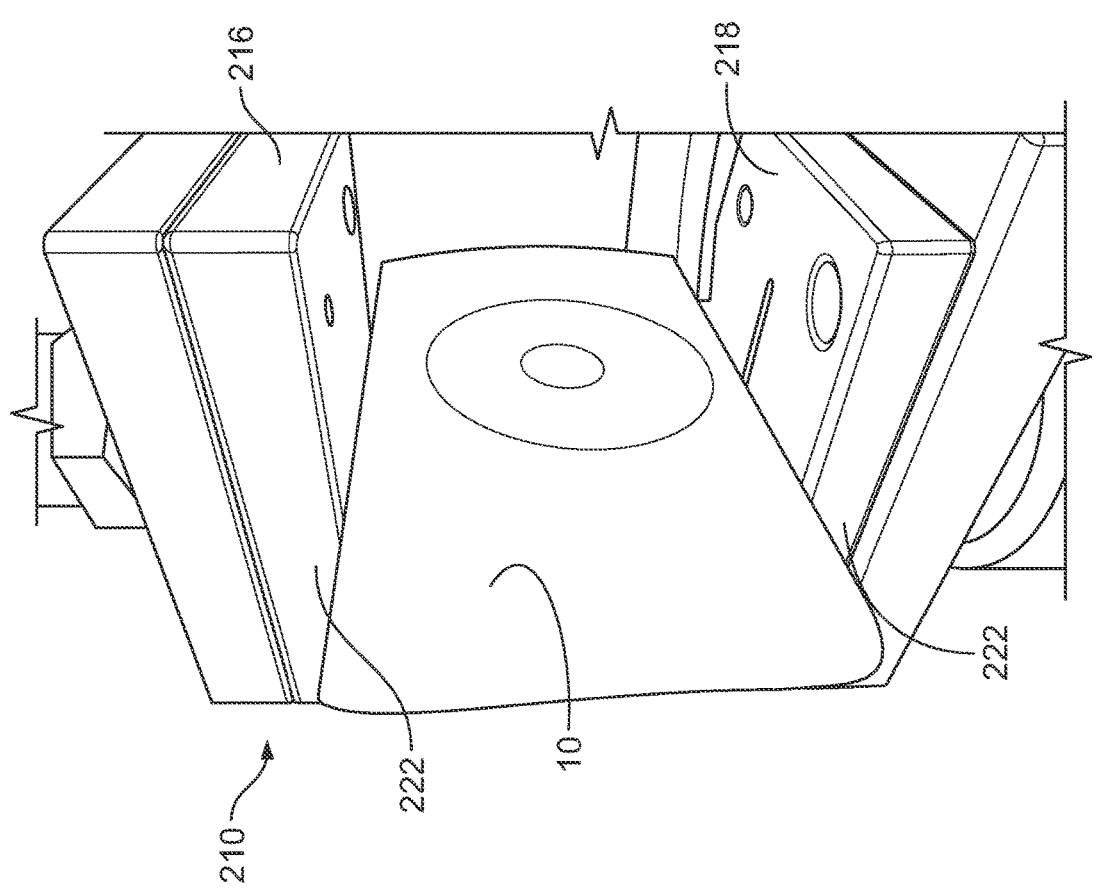

| | | | | | Compression Resistance (Softness) (N*mm) | | | | | |
|---|---|---|---|---|---|---|---|---|---|---|
| Product | Convexity | Sizing | Other Details | SKU | Insert Size Per DWG (mm) | Sample Size | Mean Energy up to 3mm | Standard Deviation | % Coefficient of Variance | Mean Compression Force (N) @ 3mm |
| Hollister 2-piece Soft Convex | Soft Convex | Small | Final Design | 11702 | 30 | 18 | 60.3 | 2.9 | 4.7% | 34.6 |
| Celicare 2-Fc Flexiconvex | Flexiconvex | Medium | 21 - 24 mm, 100mm Faceplate | 18382 | Unknown, Fits Medium Pouch | 10 | 27.3 | 0.3 | 1.2% | 16.0 |
| Mio Click Convex Light | Convex Light | Medium | Blue, Cut-to-fit, 5/8" -1-9/16" | 16921 | Unknown, Fits Medium Pouch | 10 | 37.1 | 1.1 | 3.0% | 31.2 |
| Hollister 2-piece Soft Convex | Soft Convex | Medium | Final Design | 11703 | 42 | 10 | 49.0 | 2.6 | 5.4% | 29.6 |
| Hollister 2-piece Soft Convex | Soft Convex | Medium | Blowing Agent Prototype | N/A | 42 | 15 | 54.6 | 3.3 | 6.0% | 33.8 |
| Mio Click Deep Convex | Deep Convex | Medium | Blue, Cut-to-fit, 5/8" -1-9/16" | 16961 | Unknown, Fits Medium Pouch | 10 | 44.2 | 1.7 | 3.9% | 38.2 |
| Hollister 2-piece Soft Convex | Soft Convex | Large | Final Design | 11704 | 57 | 5 | 41.5 | 3.0 | 7.2% | 23.5 |
| Hollister 2-piece Soft Convex | Soft Convex | Large | Final Design | 11704 | 57 | 18 | 46.4 | 2.1 | 4.6% | 26.2 |

FIG. 31

| | | | | | Flexibility (N*mm) | | | | |
|---|---|---|---|---|---|---|---|---|---|
| Product | Convexity | Sizing | Other Details | SKU | Insert Size per DWG (mm) | Sample Size | Mean Energy @-30% Strain | Standard Deviation | % Coefficient of Variance | Functional Parts Height (in) |
| Hollister 2-piece Soft Convex | Soft Convex | Small | Final Design | 11702 | 30 | 18 | 162.9 | 7.9 | 4.8% | 2.51 |
| Celicare 2-Fc Flexiconvex | Flexiconvex | Medium | 21 - 24 mm, 100mm Faceplate | 18382 | Unknown, Fits Medium Pouch | 10 | 164.2 | 18.4 | 11.2% | 2.81 |
| Mio Click Convex Light | Convex Light | Medium | Blue, Cut-to-fit, 5/8" -1-9/16" | 16921 | Unknown, Fits Medium Pouch | 10 | 259.3 | 6.1 | 2.4% | 2.80 |
| Hollister 2-piece Soft Convex | Soft Convex | Medium | Final Design | 11703 | 42 | 10 | 134.7 | 5.4 | 4.0% | 2.91 |
| Hollister 2-piece Soft Convex | Soft Convex | Medium | Blowing Agent Prototype | N/A | 42 | 15 | 127.7 | 3.9 | 3.1% | 2.91 |
| Mio Click Deep Convex | Deep Convex | Medium | Blue, Cut-to-fit, 5/8" -1-9/16" | 16961 | Unknown, Fits Medium Pouch | 10 | 446.0 | 13.1 | 2.9% | 2.86 |
| Hollister 2-piece Soft Convex | Soft Convex | Large | Final Design | 11704 | 57 | 5 | 124.0 | 5.3 | 4.3% | 3.53 |
| Hollister 2-piece Soft Convex | Soft Convex | Large | Final Design | 11704 | 57 | 18 | 129.8 | 8.2 | 6.3% | 3.53 |

FIG. 32

SOFT CONVEX OSTOMY APPLIANCE

This is a National Stage Application of International Patent Application No. PCT/US2020/062997 filed Dec. 3, 2020, which claims the benefit of and priority to U.S. Provisional Application No. 62/945,067 filed Dec. 6, 2019, the entirety of which are incorporated fully herein by reference.

BACKGROUND

The following description relates to an ostomy appliance, for example, 2 piece, soft convex ostomy appliance.

A known ostomy appliance includes a base plate having an adhesive wafer to which a convex insert is secured. The known ostomy appliance may also include a collecting bag. Base plates are used for attaching ostomy bags to the skin of a user having a stoma. The base plate includes a backing layer on which a skin friendly adhesive is disposed. The base plate includes a stoma opening configured to receive a stoma so that the base plate may be adhered to the skin surrounding the stoma.

The convex insert may be used in instances where the stoma is retracted or sunken into the user's body. The convex supporting device may apply pressure to the user's body in the area surrounding the stoma in such a way that the stoma may project outward and be received through the stoma opening.

However, conventional base plates having convex inserts may be relatively stiff and inflexible and thus, may not conform to a user's body or movements of the user's body. Accordingly, users may find such conventional base plates to be uncomfortable.

Soft convex base plates have been developed in an effort to improve user comfort. A known soft convex base plate may have a higher degree of flexibility than previous "stiff" convex base plates. However, increased flexibility and comfort of the soft convex base plates may negatively affect the ability to maintain a desired pressure to the user's body in the area surrounding the stoma. Thus, it may be difficult to adequately protrude the stoma.

Accordingly, it is desirable to provide an ostomy appliance, such as a 2-piece soft convex ostomy appliance having softness and flexibility characteristics within a predetermined range. For example, it may be desirable to provide a 2-piece soft convex ostomy appliance having greater flexibility than known 2-piece convex ostomy appliances while maintaining adequate softness to reliably maintain pressure in a peristomal area to protrude the stoma.

SUMMARY

In one aspect, a convex ostomy appliance having a softness of about 32.6 N*mm to about 68.9 N*mm and a flexibility of about 105.2 N*mm to about 186.6 N*mm is provided. The ostomy appliance may include a soft convex insert, an adhesive for attaching the ostomy appliance to a user, and a stoma opening configured to receive a stoma. The soft convex insert may include a body-side surface having a convex contour and a pouch-side surface. The convex contour of the body-side surface may be configured to provide a convex portion of the ostomy appliance. The coupling flange may be connected to the pouch-side surface of the soft convex insert and the adhesive may extend over the body-side surface of the soft convex insert. The softness of the ostomy appliance may be measured in energy expended to compress 3 mm of the convex portion, and the flexibility may be measured in energy expended to deform the ostomy appliance by 30%.

In an embodiment, the convex ostomy appliance may also include a coupling flange for attaching an ostomy pouch to the ostomy appliance. The coupling flange may be connected to the soft convex insert via a floating flange film configured to allow for movement of the coupling flange relative to the soft convex insert. In such an embodiment, the soft convex insert may include a recess, wherein one end of the floating flange film may be attached to the coupling flange, while another end of the floating flange film is attached to the soft convex insert in the recess.

In an embodiment, the floating flange film may include a base extending in an axial direction of the ostomy appliance and a corrugated portion extending radially in an initial condition. The corrugated portion may be connected to the coupling flange and the base may be connected to the soft convex insert in the recess. The ostomy appliance may be configured such that the base may be configured to axially offset the corrugated portion, wherein the axial offset is accommodated by the recess.

In an embodiment, the ostomy appliance may have the softness of about 35.6 N*mm to about 66.0 N*mm. In another embodiment, the ostomy appliance may have the flexibility of about 113.4 N*mm to about 178.7 N*mm.

In an embodiment, the ostomy appliance may have the softness of about 51.7 N*mm to about 68.9 N*mm and the flexibility of about 139.5 N*mm to about 186.6 N*mm. In another embodiment, the ostomy appliance may have the softness of about 54.6 N*mm to about 66.0 N*mm and the flexibility of about 147.1 N*mm to about 178.7 N*mm. In yet another embodiment, the ostomy appliance may have the softness of about 41.1 N*mm to about 64.4 N*mm and the flexibility of about 116.0 N*mm to about 150.9 N*mm.

In an embodiment, the ostomy appliance may have the softness of about 43.7 N*mm to about 61.2 N*mm and the flexibility of about 118.9 N*mm to about 145.5 N*mm. In another embodiment, the ostomy appliance may have the softness of about 32.6 N*mm to about 52.8 N*mm and the flexibility of about 105.2 N*mm to about 154.4 N*mm. In yet another embodiment, the ostomy appliance may have the softness of about 35.6 N*mm to about 50.6 N*mm and the flexibility of about 108.1 N*mm to about 146.2 N*mm.

In an embodiment, the ostomy appliance may have the softness less than about 63.2 N*mm, and the flexibility less than about 145.6 N*mm, or less than about 127.3 N*mm, or less than about 108.9 N*mm. In another embodiment, the ostomy appliance may have the softness less than about 42.4 N*mm and the flexibility less than about 127.3 N*mm.

In another aspect, a convex ostomy appliance may include a soft convex insert and a coupling flange, which are connected by a floating flange film. The soft convex insert may include a recess and a convex contour configured to provide a convex portion of the ostomy appliance. One end of the floating flange film may be secured to the coupling flange while the other end of the floating flange film may be secured to the soft convex insert in the recess. The ostomy appliance may further include an adhesive extending over the soft convex insert and a stoma opening extending through the coupling flange, the floating flange film and the soft convex insert.

In an embodiment, the floating flange film may include a base extending in an axial direction of the ostomy appliance and a corrugated portion extending radially in an initial condition. The corrugated portion may be connected to the coupling flange and the base may be connected to the soft convex insert in the recess. The ostomy appliance may be configured such that the base of the floating flange film may axially offset the corrugated portion to provide improved discretion for users, wherein the axial offset is accommodated by the recess.

In an embodiment, the ostomy appliance may have a softness of about 32.6 N*mm to about 68.9 N*mm, wherein the softness is measured in energy expended to compress 3 mm of the convex portion. The ostomy appliance may have a flexibility of about 105.2 N*mm to about 186.6 N*mm, wherein the flexibility is measured in energy expended to deform the ostomy appliance by 30%.

Other objects, features, and advantages of the disclosure will be apparent from the following description, taken in conjunction with the accompanying sheets of drawings, wherein like numerals refer to like parts, elements, components, steps, and processes.

BRIEF DESCRIPTION OF THE DRAWINGS

FIG. 3 is a side view of an ostomy appliance according to an embodiment;

FIG. 4 is a side view showing a cross-section of an ostomy appliance according to an embodiment;

FIG. 5 is a perspective view showing a cross-section of an ostomy appliance, according to an embodiment;

FIG. 6 is a perspective view of a soft convex insert according to an embodiment;

FIG. 7 is a side view showing a cross-section of a soft convex insert, according to embodiments;

FIG. 20 shows an ostomy appliance arranged in a tensile testing machine configured to perform a flexibility test, according to an embodiment;

FIG. 25 shows an example of an ostomy appliance being positioned in a tensile testing machine for a flexibility test, according to an embodiment;

FIG. 26 shows another example of an ostomy appliance being positioned in a tensile testing machine for a flexibility test, according to an embodiment;

FIG. 27 shows another example of an ostomy appliance being positioned in a tensile testing machine for a flexibility test, according to an embodiment;

FIG. 28 is a perspective view of the tensile testing machine having an ostomy appliance arranged for a flexibility test, according to an embodiment;

FIG. 31 is a table showing softness test results for differently sized ostomy appliances according to present embodiments and other commercial ostomy appliances;

FIG. 32 is a table showing flexibility test results for differently sized ostomy appliances according to present embodiments and other commercial ostomy appliances;

DETAILED DESCRIPTION

Figure 1:
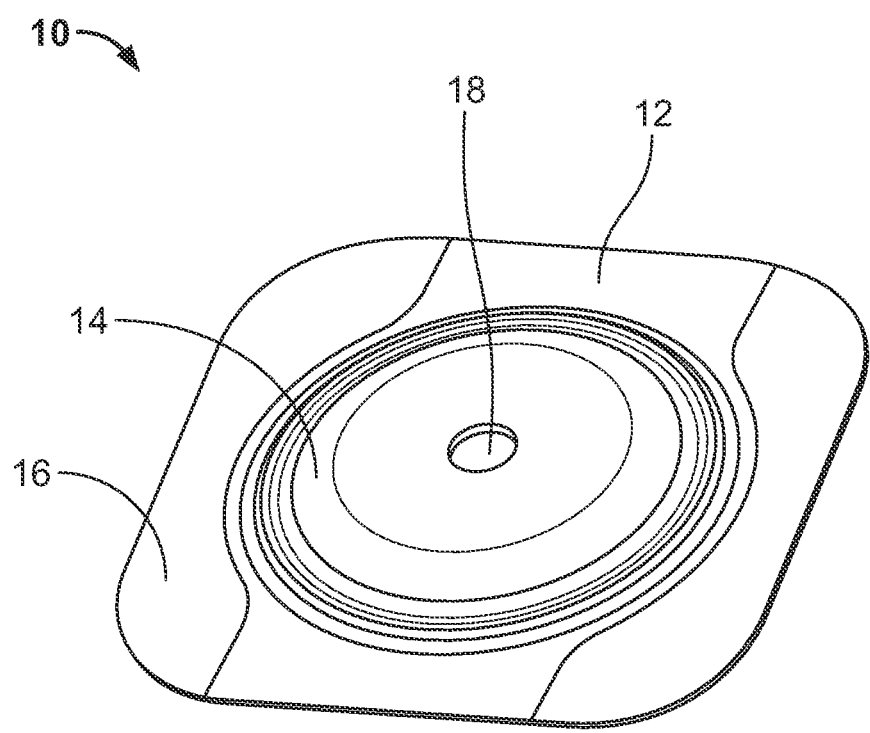
FIG. 1 is a perspective view of an ostomy appliance according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a perspective view of an ostomy appliance 10 according to an embodiment. The ostomy appliance may be a base plate configured for detachable connection to an ostomy pouch (not shown). The ostomy appliance 10 may have a body-facing side 12 configured to be secured to a user's body (not shown). The ostomy appliance 10 may also include a convex portion 14 on the body-facing side 12. The convex portion 14 may be at least partially surrounded by an outer flange 16 configured to attach to the user's body at an area around the stoma, for example, with an adhesive. The ostomy appliance 10 may also include a stoma opening 18 through which a stoma may at least partially extend.

Figure 2:
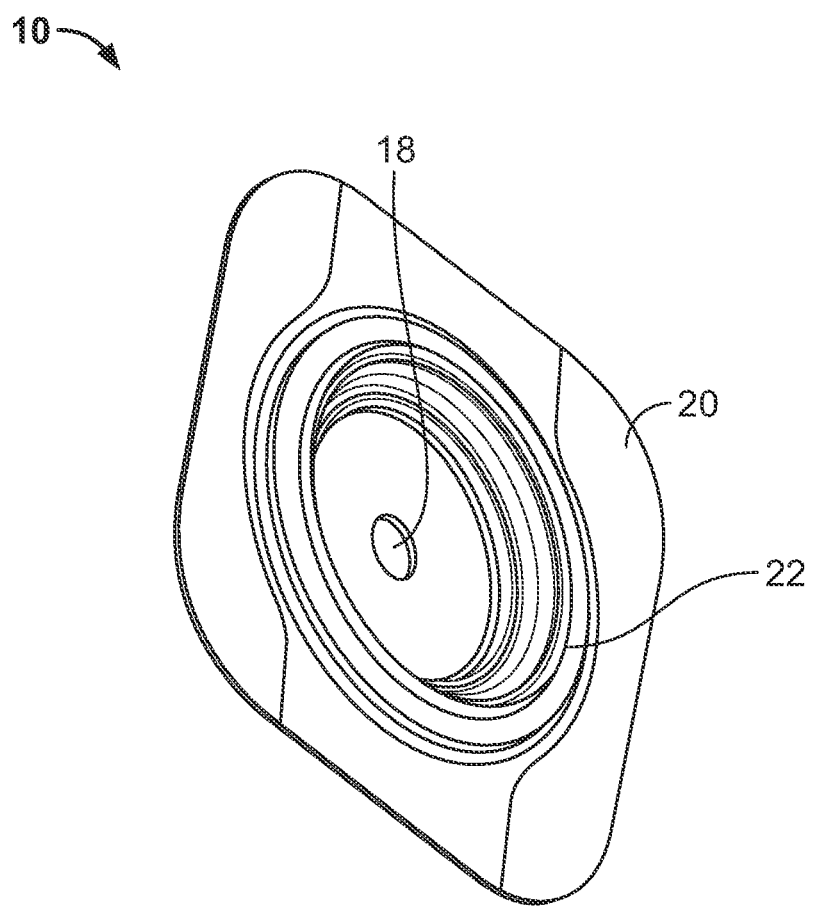
FIG. 2 is another perspective view of an ostomy appliance, according to an embodiment.

FIG. 2 is another perspective view of the ostomy appliance 10, according to an embodiment. The ostomy appliance 10 may also include a pouch-facing side 20 configured to be connected to an ostomy pouch (not shown). For example, the ostomy appliance 10 may include a coupling flange 22 on the pouch-facing side 20, to which the ostomy pouch may be coupled. The stoma opening 18 may extend through the ostomy appliance 10 from the body-facing side 12 to the pouch-facing side 20. Accordingly, effluent from the stoma may be received in an ostomy pouch (not shown) connected to the ostomy appliance 10.

FIG. 3 is a side view of the ostomy appliance 10 according to an embodiment. As described above with reference to FIGS. 1 and 2, the ostomy appliance 10 may include the convex portion 14 on the body-facing side 12. The outer flange 16 may be disposed radially outward of the convex portion 14. The ostomy appliance 10 may also include the coupling flange 22 on the pouch-facing side 20. In an embodiment, the convex portion 14 and the coupling flange 22 may be aligned or substantially aligned on an axis 'A' extending in an axial direction of the ostomy appliance 10.

FIG. 4 is a side view showing a cross-section of the ostomy appliance 10 and FIG. 5 is a perspective view showing a cross-section of the ostomy appliance 10, according to embodiments. The ostomy appliance 10 may include the coupling flange 22, a floating flange film 24, a soft convex insert 26 and an adhesive 28. In an embodiment, the coupling flange 22, the floating flange film 24, the soft convex insert 26 and the adhesive 28 may be arranged in series from the pouch-facing side 20 to the body-facing side 12. In an embodiment, the convex portion 14 of the ostomy appliance 10 may be formed, at least partly, by the soft convex insert 26. The soft convex insert 26 may be at least partially covered by the adhesive barrier 28 on the body-facing side 12. The stoma opening 18 may extend completely through the ostomy appliance 10. For example, the stoma opening 18 may include respective openings in the adhesive 28, the soft convex insert 26, the floating flange film 24 and the coupling flange 22. The stoma may be received into the stoma opening 18 through the adhesive 28.

The coupling flange 22 may include a coupling part 30 configured for selectively connecting the ostomy pouch (not shown) to the coupling flange 22. For example, as also shown in FIG. 2, the coupling part 30 may be a substantially annular fastener configured for interlocking connection with a corresponding fastener of an ostomy pouch. The coupling flange 22 may also include a web 32 for connecting the coupling flange 22 to the floating flange film 24. The coupling flange 22 may be made from an injection moldable material.

The floating flange film 24 may be connected between the coupling flange 22 and the soft convex insert 26. The floating flange film 24 may have a base 34 and a corrugated portion 36. The base 34 may be connected to the soft convex insert 26 using a known, suitable fastening technique, such as heat sealing, welding, adhesive, mechanical fasteners and the like. The base 34 may extend generally in an axial direction of the ostomy appliance 10, for example, in a direction of the axis 'A.' The corrugated portion 36 may extend generally radially relative to the axis 'A' in an initial condition. The corrugated portion 36 may be connected to the coupling flange 22, for example to the web 32 of the coupling flange 22, using a known, suitable fastening technique, such as a heat sealing, welding, adhesive, mechanical fasteners and the like. In an embodiment, the corrugated portion 36 may extend generally in an outward radial direction from the base 34.

FIG. 6 is a perspective view of the soft convex insert 26 and FIG. 7 is a side view showing a cross-section of the soft convex insert 26 according to embodiments. With reference to FIGS. 6 and 7, the soft convex insert 26 may include a foot 38 and a body 40. The foot 38 and the body 40 may be formed integrally and continuously with another, as one-piece, for example, in a molding process such as injection molding. Accordingly, the soft convex insert 26 may be a one-piece construction. The soft convex insert 26 may be annular in shape and may include an opening which may form at least a portion of the stoma opening 18.

In an embodiment, the foot 38 may have a substantially concave outer profile. The body 40 may have a substantially convex outer profile to provide, at least in part, the convex portion 14 on the body-facing side 12. In an embodiment, an inner diameter D1 of the soft convex insert 26 may be provided as a diameter of an inner wall 42 of the body 40 surrounding the stoma opening 18. In an embodiment, and outer diameter D2 of the soft convex insert 26 may be provided as the diameter of the outer periphery 44 of the foot 38.

The soft convex insert 26 may also include a recess 46 along an inner periphery adjacent to, and/or axially spaced from, the inner wall 42. The recess 46 may be formed, at least in part, by a radial shoulder 48 and an axial shoulder 50. The recess 46 may have a recess diameter D3 provided as the inner diameter of the radial shoulder 48. In an embodiment, the inner diameter D1 may be less than the recess diameter D3, and the recess diameter D3 may be less than the outer diameter D2.

In an embodiment, the soft convex insert 26 may have a first height H1, provided as a distance in the axial direction from an end of the soft convex insert 26 nearest the pouch-facing side 20 to an end of the soft convex insert 26 nearest the body-facing side 12. The recess 46 may have a second height H2, provided as a distance in the axial direction from an end of the soft convex insert 26 nearest the pouch-facing side 20 to the axial shoulder 50. The first height H1 may be greater than the second height H2. In an embodiment, the first height H1 may be between about 3 mm and 12 mm. In an embodiment, the first height H1 may be between about 4 mm and 9 mm. In an embodiment, the first height H1 may be approximately 6 mm. In one embodiment, the second height H2 may be any height less than the first height H1. In an embodiment, the second height H2 may be between about 1 mm and 11 mm. In an embodiment, the second height H2 may be between about 2 mm and 8 mm. In an embodiment, the second height H2 may be approximately 3 mm.

In an embodiment, the soft convex insert 26 may also include an annular lip 52. The annular lip 52 may extend radially inward relative to the inner wall 42, and thus, may have a diameter less than the inner diameter D1. In an embodiment, the inner diameter D1 may be provided as the inner diameter of the annular lip 52. The annular lip 52 may be positioned at or near an end of the soft convex insert 26 nearest the body-facing side 20. Referring to FIGS. 4-7, the floating flange film 24 may be connected to the soft convex insert 26 in the recess 46. For example, the base 34 may be connected to axial shoulder 50.

The soft convex insert 26 may be made from flexible polymer materials. In an embodiment, the soft convex insert 26 may be formed from ethylene-vinyl acetate copolymer, such as ELVAX® 450 from DuPont.

Referring again to FIGS. 3-5, the adhesive 28 may extend over the soft convex insert 26 at the body-facing side 12 of the ostomy appliance 10. The adhesive 28 may include an adhesive layer 54 on the body-facing side 12 for adhering to the user's body and a backing layer 56 on the pouch-facing side 20. The adhesive 28 may also include a release sheet removably disposed on the body-facing side 12 configured to protect the adhesive layer 54 prior to use. In an embodiment, the adhesive layer 54 may extend over the convex portion 14. The backing layer 56 may form at least a portion of the outer flange 16. In an embodiment, the backing layer 56 may also include an adhesive on the body-facing side 12 for adhering to the user's skin. In an embodiment, the adhesive layer 54 may be a different adhesive than an adhesive of the backing layer 56 on the outer flange 16. Suitable adhesives include suitable medical-grade adhesives that can adhesively secure the ostomy appliance to the patient's skin in the peristomal region, such as a hydrocolloid adhesive composition.

The stoma opening 18 in the adhesive 28 may be manufactured at a predetermined size, e.g., diameter. Different ostomy appliances 10 may have differently sized stoma openings 18 in the adhesive wafer 28. Accordingly, a user may select an ostomy appliance 10 having an appropriately sized stoma opening 18. Alternatively, or in addition, the stoma opening 18 in the adhesive 28 may be sized by the user, for example, by cutting or punching. Thus, a user may select an ostomy appliance 10 and size the stoma opening 18, e.g., by cutting or punching, to provide an appropriately sized stoma opening 18.

Figure 8:
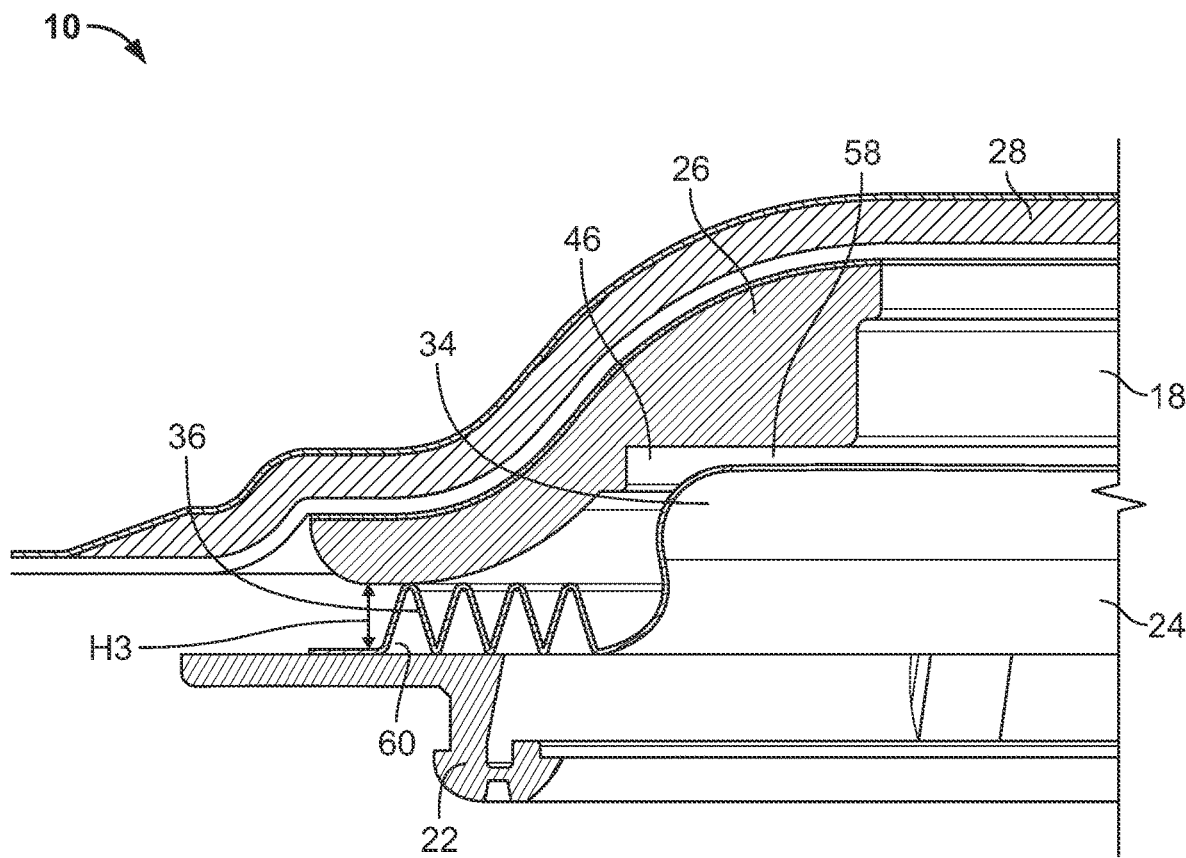
FIG. 8 is an enlarged side view showing a cross-section of a portion of an ostomy appliance, according to an embodiment.

FIG. 8 is an enlarged side view showing a cross-section of a portion of the ostomy appliance 10 according to an embodiment. The floating flange film 24 is configured to allow for movement of the coupling flange 22 relative to the soft convex insert 26 and the adhesive 28. Such movement may be accommodated by connecting one portion of the floating flange film 24 to the soft convex insert 26 and another portion of the floating flange film 24 to the coupling flange 22. For example, as described above, a base 34 of the floating flange film may be connected in the recess 46 of the soft convex insert 26 and an opposite end may be connected to coupling flange 22. In an embodiment, the floating flange film 24 may have a fixed end 58 connected to the soft convex insert 26 and a floating end 60 connected to the coupling flange 22.

In the embodiments described above, an ostomy appliance 10 is provided with a floating coupling flange 22, which may allow for movement of the coupling flange 22 relative to the soft convex insert 26 and adhesive 28. Accordingly, movements of the coupling flange 22 which, for example, may correspond to movements of the user's body, may provide improved comfort to user. Alternatively, or in addition, movements of the coupling flange 22 may allow a user to more easily manipulate the coupling flange 22, for example, to attach and/or remove an ostomy pouch.

Moreover, in the embodiments described herein, the base 34 of the floating flange film 24 may be axially offset from the corrugated portion 36. The axial offset may be accommodated by the recess 46 in the soft convex insert 26 in which the base 34 is connected. Thus, an axial space between the attachment surface of the coupling flange 22 and the soft convex insert 26 provides an area in which the corrugated portion 36 may be contained to provide improved discretion. For example, when extended, the second height H2 may offset a distance between the pouch-facing surface of the face plate and the pouch, which may thereby reduce sagging of the pouch from the face plate.

Comfort of the ostomy appliance 10, when worn by the user, may depend on several characteristics, such as flexibility (sometimes referred to as bending resistance) and softness (sometimes referred to as compression resistance). These same factors may also affect performance of the ostomy appliance. For example, a user may find an ostomy appliance that is relatively flexible (i.e., a relatively low bending resistance) and relatively soft (i.e., a relatively low compression resistance) to be very comfortable. However, with increased flexibility and/or increased softness, a convex portion may not provide sufficient pressure against a user's skin to cause the stoma to adequately protrude. In such instances, effluent from the stoma may come into contact with the user's skin and/or the adhesive on a body-facing side of the ostomy appliance. Such contact may lead to skin irritation and user discomfort, and/or reduced wearable time of the ostomy appliance.

In the present description, the term "softness" is used to describe a compression resistance of the ostomy appliance 10 when a force is applied to the convex portion 14 with the ostomy appliance 14 laid flat on its pouch-facing side 20. The softness of the ostomy appliance is provided as a unit of energy, such as N*mm, calculated as an area under a force vs. displacement curve. That is, in present embodiments, softness may refer the energy expended to displace or compress the convex portion 14 a predetermined distance. The term "flexibility" is used herein to describe a bending resistance of an ostomy appliance 10 arranged vertically, i.e., with a diameter of the coupling flange 22 and/or soft convex insert 26 on a vertical axis, when a compressive force is applied to the ostomy appliance 10 on the vertical axis. The flexibility is provided as a unit of energy, such as N*mm, calculated as an area under a force vs. displacement curve. That is, in present embodiments, flexibility may refer to the energy expended to strain the ostomy appliance 10 by a predetermined amount. For example, flexibility may refer to the energy expended to deform the vertically arranged ostomy appliance 10 by 30%, i.e., so that the height of the vertically arranged ostomy appliance 10 is reduced by 30% by application of the compressive force.

Embodiments of the present ostomy appliance 10 described herein may avoid such outcomes by providing flexibility and/or softness characteristics which may provide increased comfort to a user relative to prior art ostomy appliances, while maintaining desirable performance characteristics. For example, in the present embodiments, the ostomy appliance 10 having the soft convex insert 26 has shown to exhibit optimal combinations of flexibility and softness to provide improved comfort and performance when compared to known ostomy appliances.

Figure 9:
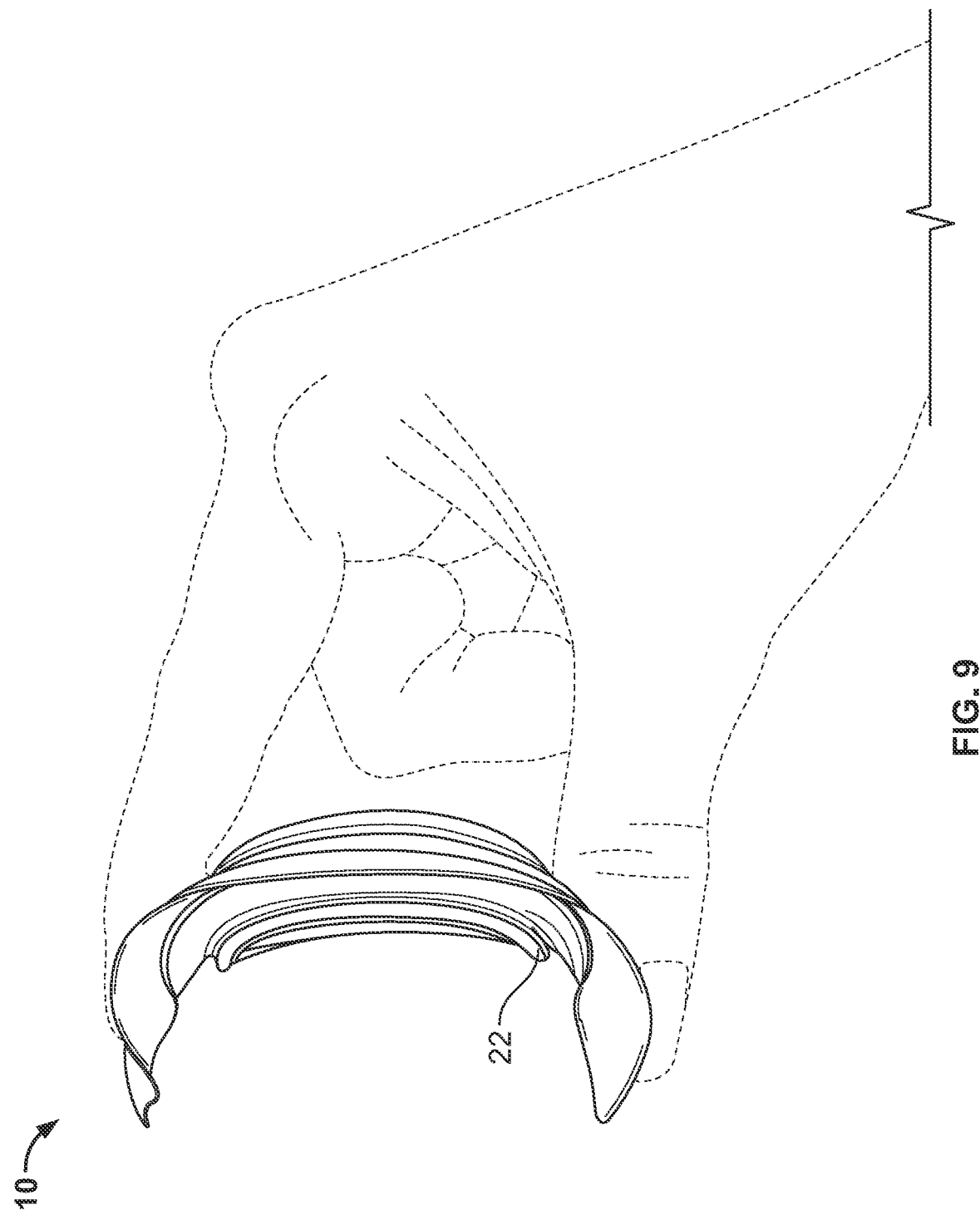
FIG. 9 is an example showing flexibility of an ostomy appliance.
Figure 10:
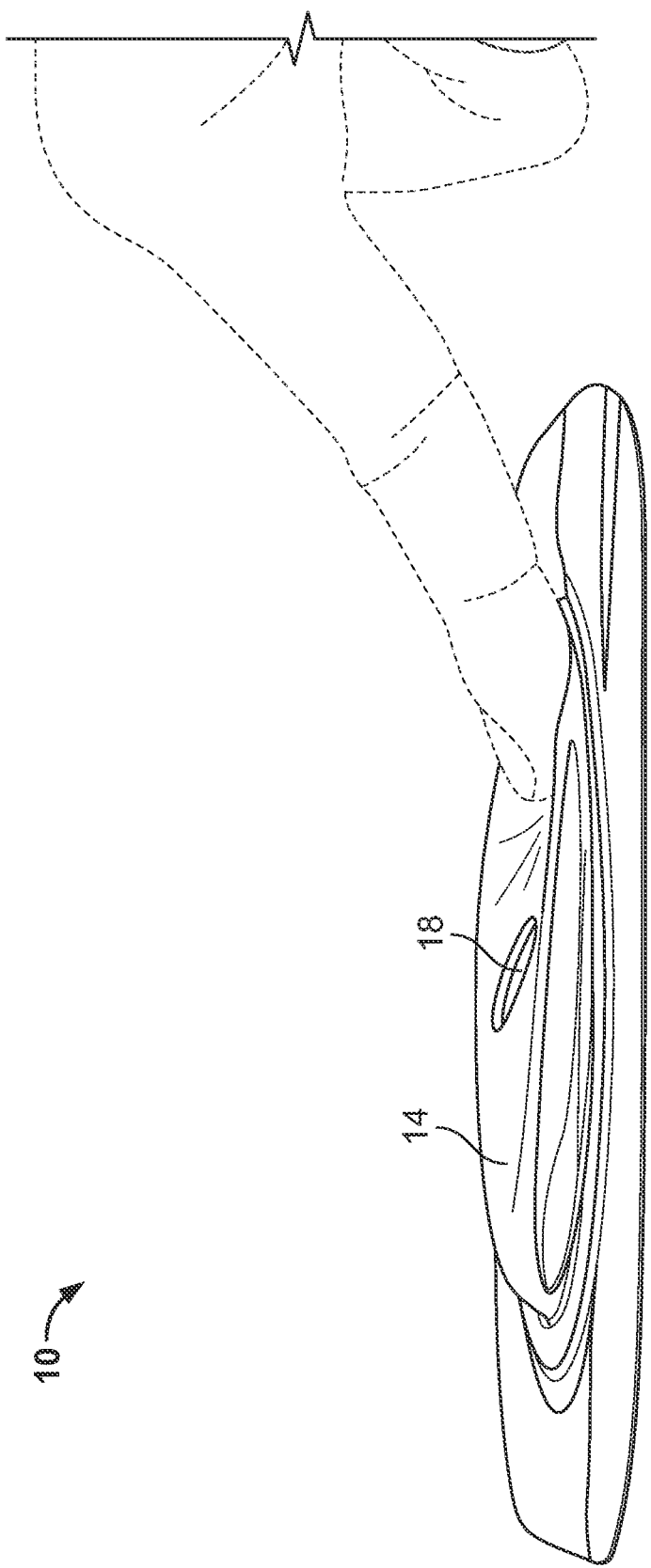
FIG. 10 is an example showing softness of an ostomy appliance.

FIG. 9 is an example showing flexibility of the ostomy appliance 10 according to an embodiment. FIG. 10 is an example showing softness of the ostomy appliance 10 according to an embodiment. The ostomy appliance 10 described above was tested for flexibility and softness according to the following test methods.

According to present embodiments, a test method for softness (compression resistance) of the ostomy appliance 10 may generally be performed by measuring a force and energy to compress the convex portion 14 of the ostomy appliance 10 over a fixed distance. The test method for measuring softness may be performed using a tensile testing machine, such as an MTS tensile testing machine.

Figure 11:
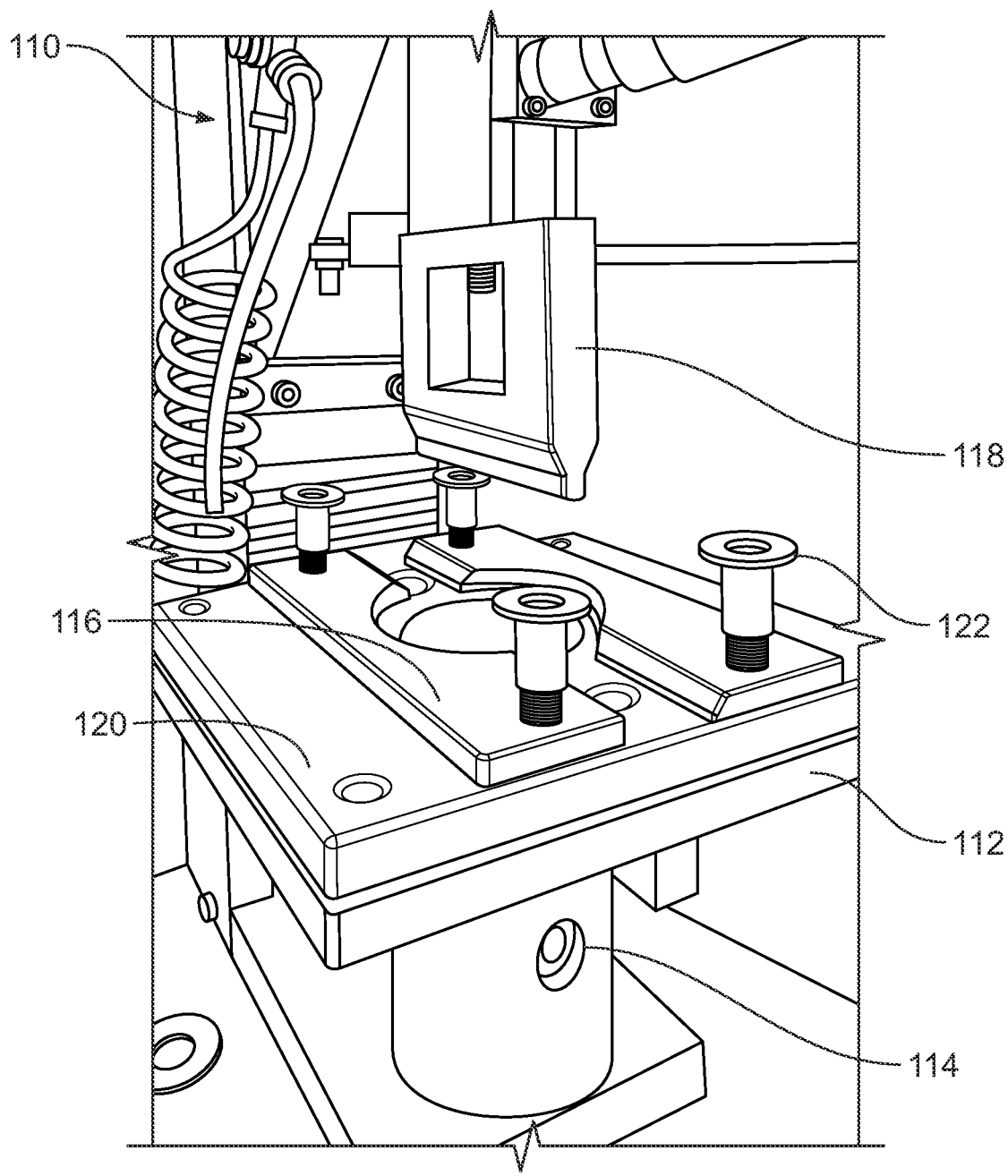
FIG. 11 shows an example of a tensile testing machine configured to perform a test method for measuring softness of an ostomy appliance.

FIG. 11 shows an example of a tensile testing machine 110 configured to perform the softness test method for an ostomy appliance. The tensile testing machine 110 may include a base platen 112 having an adapter 114, one or more securement plates 116 disposed on the base platen 112, a load cell 118, a platen insert 120 and one or more securement pins 122.

Figure 12:
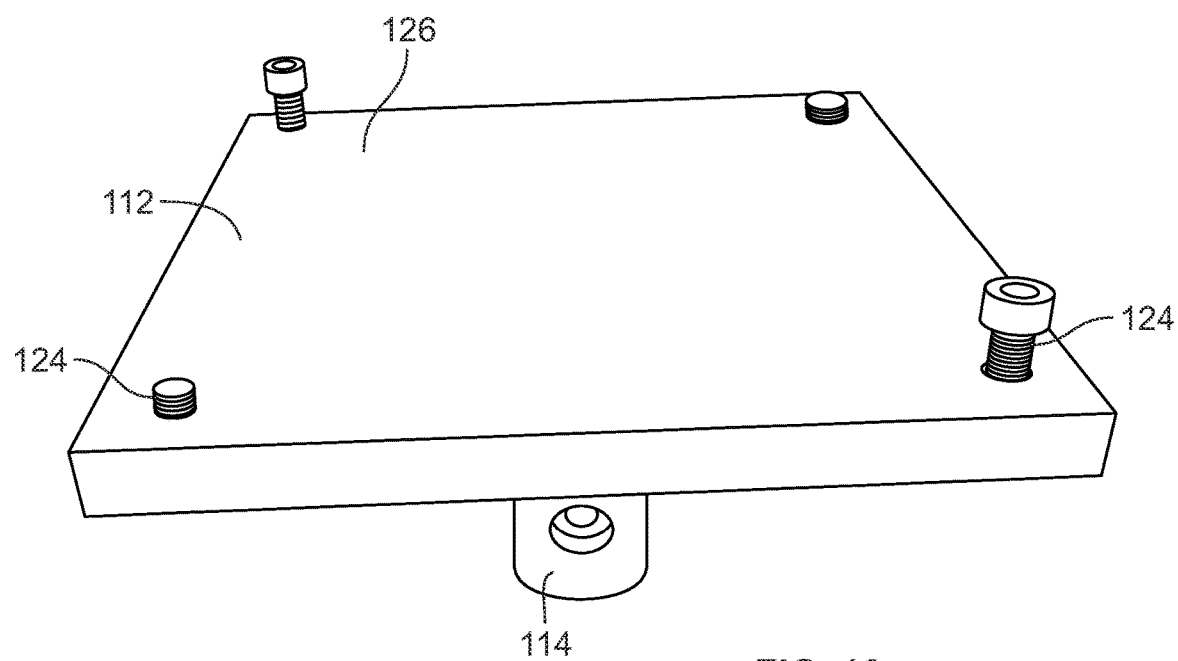
FIG. 12 is a perspective view of a base platen and an adapter of a tensile testing machine, according to an embodiment.

FIG. 12 is a perspective view of the base platen 112 and the adapter 114. The base platen 112 may include a plurality of fastening holes configured to receive corresponding fasteners 124. The fasteners 124 may be configured to attach the securement plate or plates 116 to the base platen 112. The fasteners 124 may be, for example, bolts, pins, or other known suitable fasteners or combinations of different fasteners. The base platen 124 may have a substantially flat, planar support surface 126. The adapter 114 may be configured to attach the base platen 112 to a base of the tensile testing machine 110.

Figure 13:
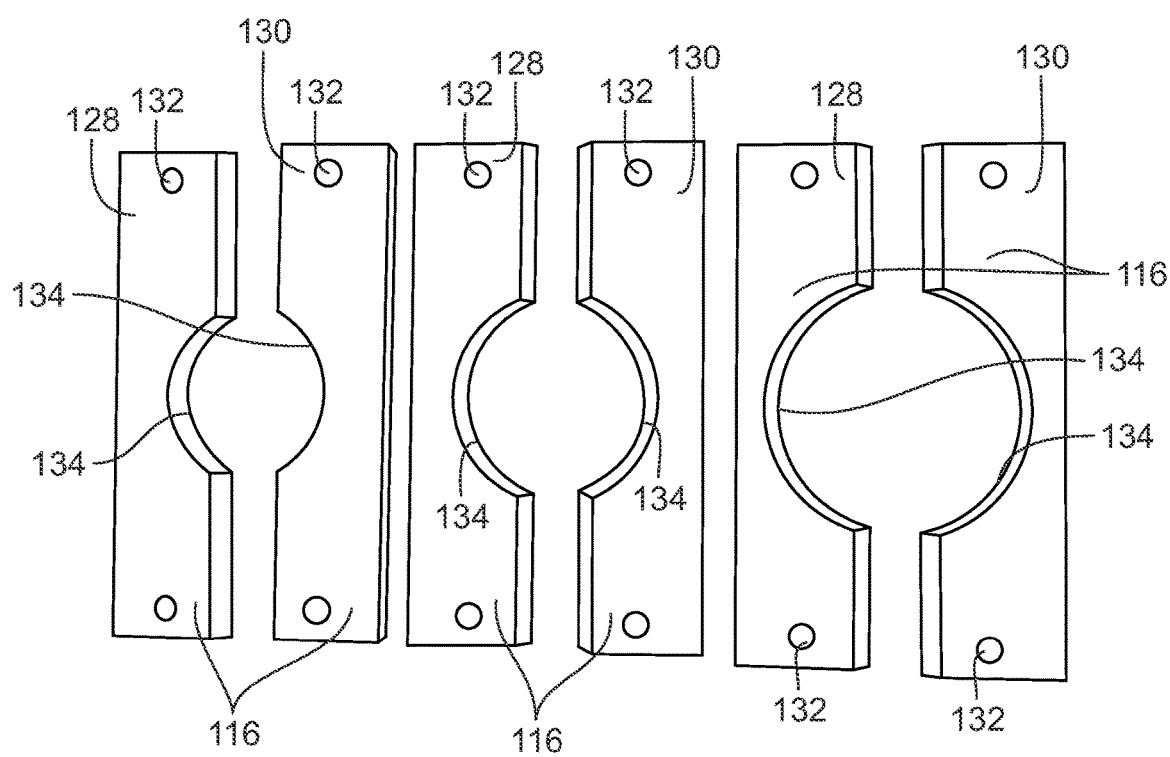
FIG. 13 shows examples of differently sized securement plates of a tensile testing machine, according to an embodiment.

FIG. 13 shows examples of differently sized securement plates 116 according to an embodiment. Each securement plate 116 may be a two-piece plate, with pieces being substantially mirror images of one another. For example, each securement plate 116 may include a first piece 128 and a second piece 130. Each piece 128, 130 may include one or more plate fastener holes 132 and a semi-circular opening 134. The securement plates 116 may be differently sized according to a diameter of the semi-circular openings 134. The semi-circular openings 134 may be sized to corresponds to different sizes of ostomy appliances 10. For example, the semi-circular openings 134 may correspond to the size (diameter) of the convex portion 14 and/or soft convex insert 26 of the ostomy appliance to be tested. Accordingly, the securement plates 116 may be configured to constrain a radially outer portion of the ostomy appliance 10, such as the outer flange 16, without constraining the convex portion 14.

Figure 14:
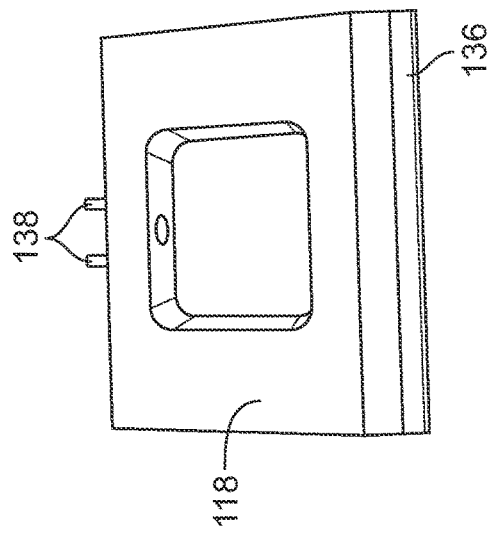
FIG. 14 shows an example of a load cell of a tensile testing machine, according to an embodiment.

FIG. 14 shows an example of the load cell 118 according to an embodiment. The load cell 118, or load cell end effector, may be a top fixture on the tensile testing machine 110, i.e., mounted above the base platen 112, and configured to be moved toward the base platen 112 along an axis during a test. In one embodiment, the load cell 118 may have a width of 5 mm at a contact end 136 configured to compress the ostomy appliance 10 during the softness test. The load cell 118 may be attached to the tensile testing machine 110 using two load cell fasteners 138 to maintain radial alignment.

Figure 15:
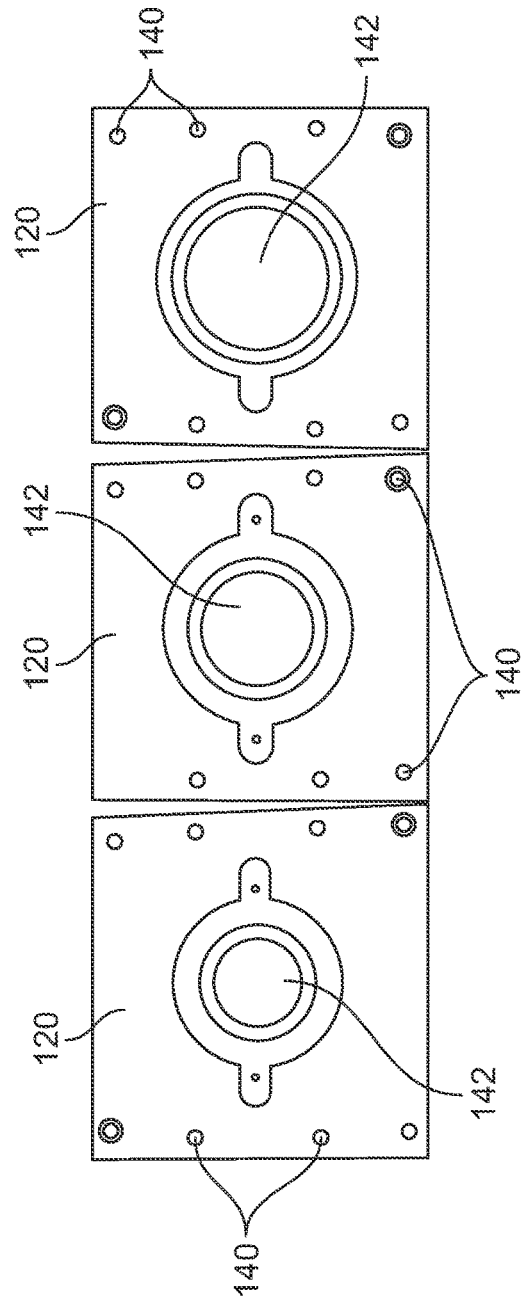
FIG. 15 shows examples of differently sized platen inserts, according to an embodiment.

FIG. 15 shows examples of differently sized platen inserts 120, according to an embodiment. Each platen insert 120 may include a plurality of platen insert fastener openings 140 and an opening 142. The opening 142 may be a circular opening, and the differently sized platen inserts 120 may be sized according to a diameter of the opening 142. Differently sized platen inserts 120, i.e., platen inserts 120 having differently sized openings 142 may be used for testing differently sized ostomy appliances 10. In one embodiment, the openings 142 may be sized to receive the coupling flange 22 of differently sized ostomy appliances 10.

Figure 16:
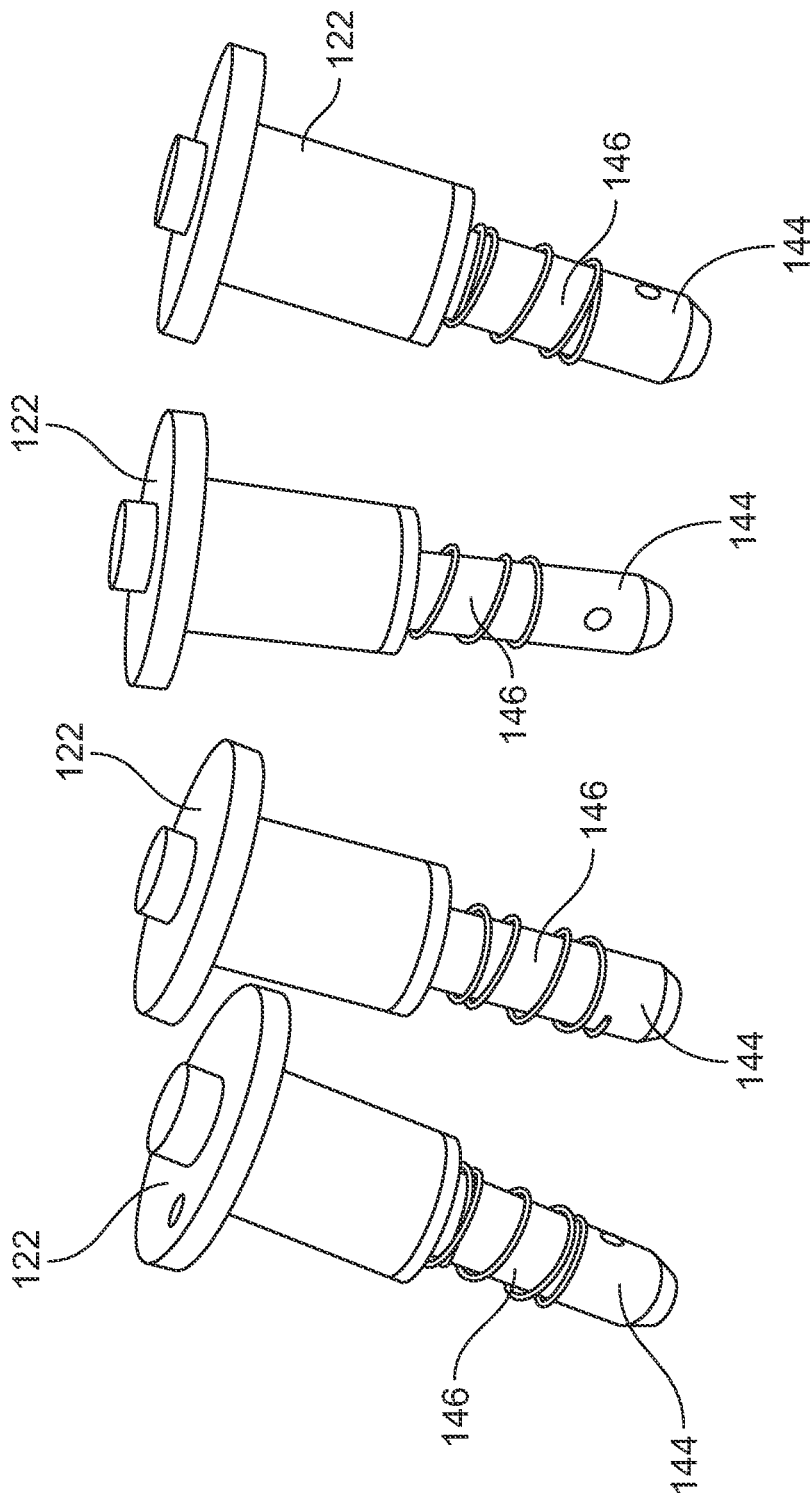
FIG. 16 shows examples of the securement pins, according to an embodiment.

FIG. 16 shows examples of the securement pins 122. The securement pins 122 may be configured to secure the securement plate 116 to the platen insert 120. In one embodiment, four securement pins 122 may be used such that each of the first piece 128 and the second piece 130 of the securement plate 116 is fastened to the platen insert 120 using two securement pins 122. The securement pins 122 may extend into or through, for example, one or more platen insert fastener openings 140 and one or more aligned support plate fastener holes 132. Each securement pin 122 may include a shank 144 and a removable spring 146 on the shank 144 so that the securement springs 122 may accommodate different heights of the convex ostomy appliance 10.

Figure 17:
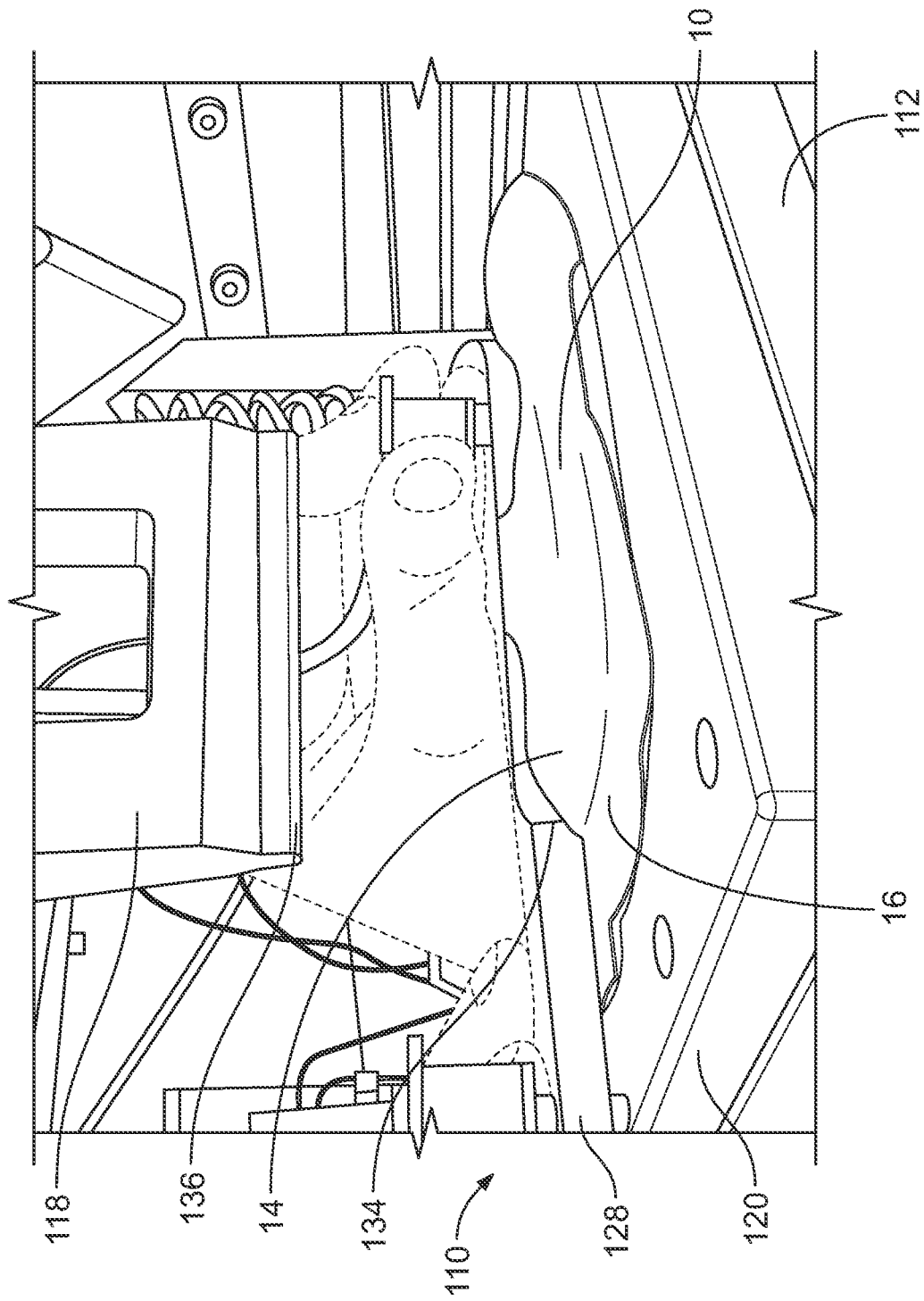
FIG. 17 shows an ostomy appliance arranged on a tensile testing machine during setup for a softness test, according to an embodiment.

FIG. 17 shows an ostomy appliance 10 arranged on the tensile testing machine 110 during setup for a softness test, according to an embodiment. A platen insert 120 may be selected based on the size of the ostomy appliance 10 to be tested. The platen insert 120 may be disposed on/or attached to the base platen 112. The ostomy appliance 10 may be positioned on the platen insert 120 such that the convex portion 14 is substantially aligned with and extends over or across the opening 142. The securement plate 116 may also be selected based on the size of the ostomy appliance 10 to be tested. The first piece 128 of the securement plate 116 may be disposed over a portion of the outer flange 16. The semi-circular opening 134 of the first piece 128 may fit around a peripheral portion of the convex portion 14. Although not shown in FIG. 17, it is understood that the second piece 130 of the securement plate 116 may be disposed over another portion of the outer flange 16 and that the semi-circular opening 134 of the second piece 130 may fit around another peripheral portion of the convex portion 14. Accordingly, the convex portion 14 on a body-facing side 12 of the ostomy appliance 10 may be exposed in the semi-circular openings 134. At least a portion of the outer flange 16 may be disposed between the first piece 128 and the platen insert 120 and the second piece 128 and the platen insert 120. In this manner, the ostomy appliance 10 may be held for the softness testing method to be performed.

Figure 18:
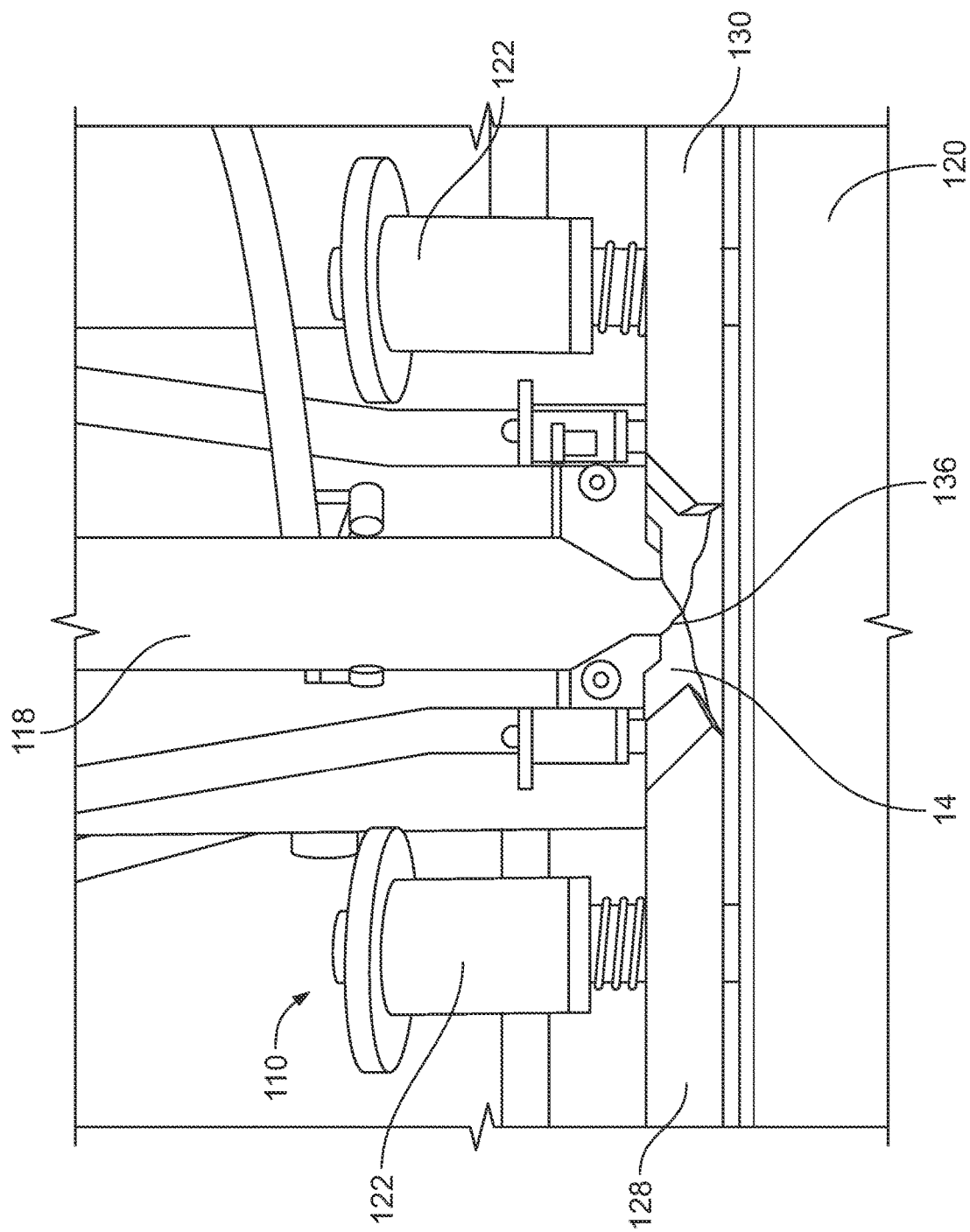
FIG. 18 is a side view of an ostomy appliance arranged on a tensile testing machine during a softness test, according to an embodiment.

FIG. 18 is a side view of an ostomy appliance 10 arranged on the tensile testing machine 110 during the softness test method. In one embodiment, the first piece 128 and the second piece 130 of the securement plate 116 may be disposed over respective portions of the outer flange 16 of the ostomy appliance. The first piece 128 and the second piece 130 may be connected to the platen insert 120 with the securement pins 122. The convex portion 14 of the ostomy appliance 10 may be disposed semi-circular openings 134 of the first piece 128 and the second piece 130, and thus, may be exposed. The contact end 136 of the load cell 118 may be moved into contact with the convex portion 14 during the softness test method.

The ostomy appliance 10 may be prepared for the softness test method by removing a release liner and replacing with a lint-free wipe, such as KIMWIPE, or similar. The ostomy appliance 10 may be placed on the platen insert 120 in the manner described above. The securement plate 116 is configured to constrain a perimeter of the ostomy appliance 10, e.g., the outer flange 16, around the convex portion 14 without touching the convex portion 14, to mimic how the ostomy appliance 10 would be constrained on a user. The load cell 118 may be lowered into contact with the convex portion 14 to apply a preload of about 0.4 N.

The load cell 118 may be controlled to move at a rate of 5 inches per minute to compress the convex portion 14. The load cell 118 may be moved through a fixed displacement of 3.0 mm (about 0.118 in.). The tensile testing machine 110 may include, or be operably connected to, a computer configured to execute software for recording and/or calculating basic statistics during the softness test method. For example, the tensile testing machine 110 may record, with the computer, the force applied at the load cell 118 at different displacements during the softness test method. The tensile testing machine 110, at the computer, may also determine other information, such as mean, minimum, maximum, standard deviation, and % coefficient of variance for record values. The tensile testing machine 110 may also calculate the energy from Oto 1 mm displacement, 1 to 2 mm, and 2 to 3 mm (area under the force v. displacement curve). Further, the tensile testing machine 110 may calculate or record the compression force at 3 mm displacement and/or the compression distance at 5 N of force. It is understood that the computer for executing the software for recording and/or calculating may be part of the tensile testing machine 110 or a peripheral computing device operably connected to the tensile testing machine 110 or capable of receiving force and displacement information from the tensile testing machine 110.

The softness test method may be performed on ostomy appliances of different sizes. For example, the softness test method above was performed on ostomy appliances having 1.75 in. coupling flange inner diameter, a 2.25 in. coupling flange inner diameter, and 2.75 in. coupling flange inner diameter (which also may be referred to as "small," "medium" and "large" appliances in this disclosure). The softness test method may be performed on other 2-piece ostomy appliances having a convex insert as well, which may vary in size from the examples above. In such instances, the tensile testing machine 110 and related components may be adapted as closely as possible in an effort to provide substantially similar testing environments so that test results may be reliably compared. The softness test method may be performed on the ostomy appliance 10 having the coupling flange 22, the flexible flange film 24, the soft convex insert 26 and the adhesive 28, without a pouch attached to the coupling flange 22.

Figure 19:
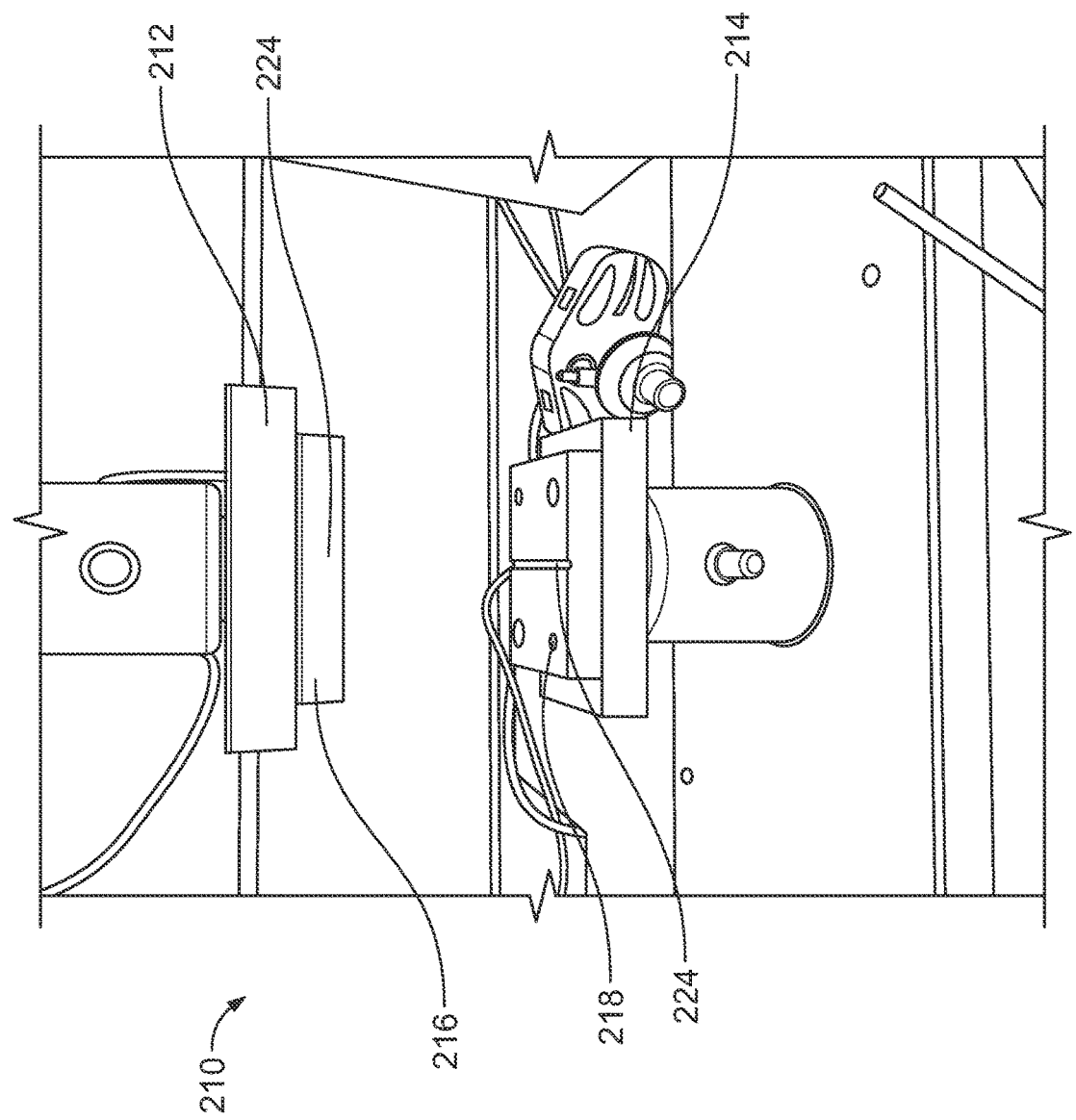
FIG. 19 shows a portion of a tensile testing machine for performing a flexibility test, according to an embodiment.

FIGS. 19-30 are directed to a flexibility test method for an ostomy appliance 10, according to an embodiment. FIG. 19 shows a portion of a tensile testing machine 210 for performing a flexibility test method according to an embodiment. The tensile testing machine 210 may include an upper platen 212 and a lower platen 214. An upper platen insert 216 may be attached to the upper platen 212. The lower platen insert 218 may be attached to the lower plate 218. The upper platen 212 may be moved toward the lower platen 214, or vice versa to perform the flexibility test method. The tensile testing machine 210 may include test works software or equivalent, or be operably coupled to a computing device having test works software or equivalent. The tensile testing machine 210 may provide a constant rate of traverse when one platen moves toward the other.

FIG. 20 shows an ostomy appliance 10 arranged on the tensile testing machine 210 for performing the flexibility test method. The ostomy appliance 10 may be prepared such that injection-molded portions, for example, the coupling flange 22, are disposed in contact with the platen inserts 216, 218.

Figure 22:
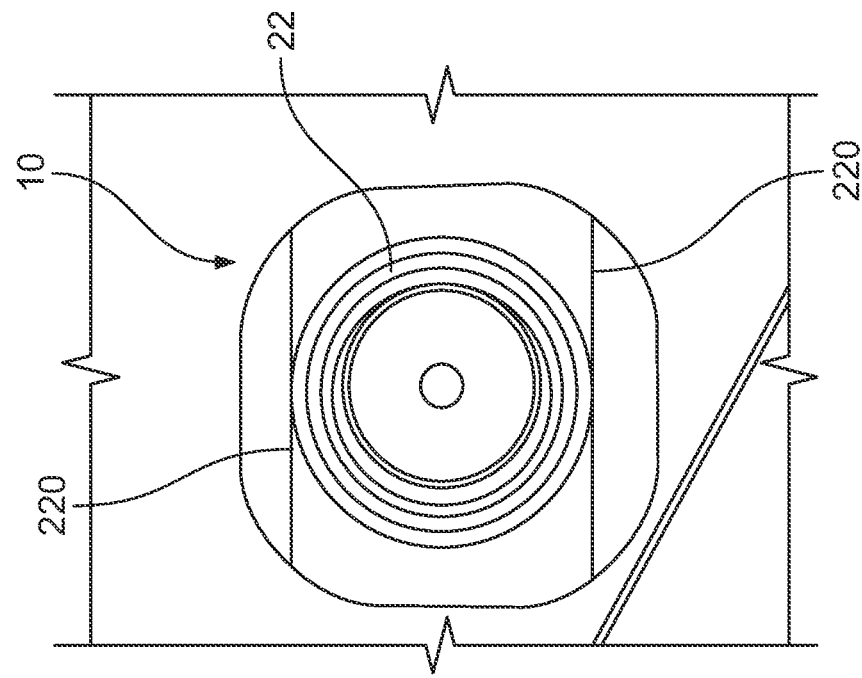
FIG. 22 shows another example of an ostomy appliance being prepared for a flexibility test, according to an embodiment.
Figure 21:
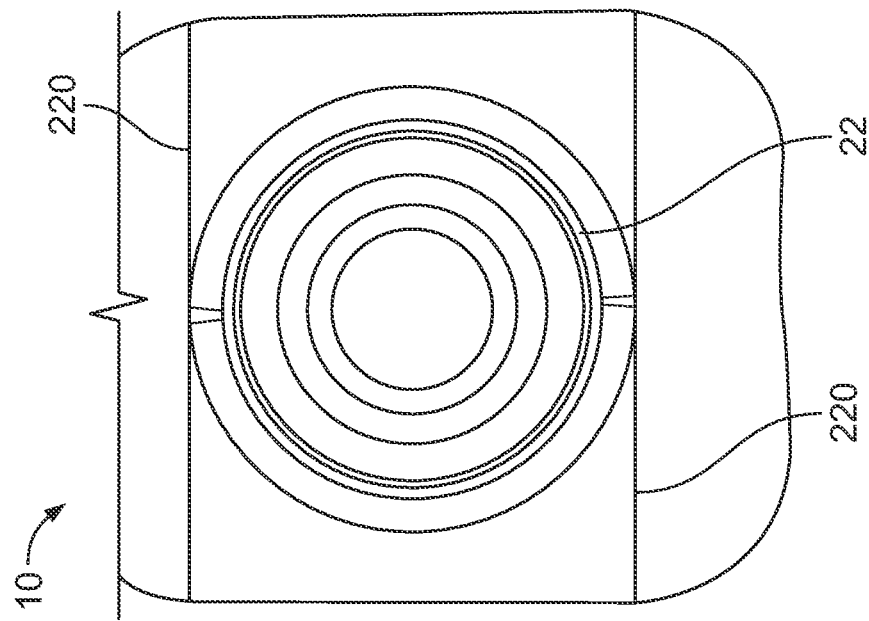
FIG. 21 shows an example of an ostomy appliance being prepared for a flexibility test, according to an embodiment.

FIGS. 21 and 22 show examples of ostomy appliances 10 being prepared for the flexibility test method. In one embodiment, to prepare the ostomy appliance 10 for the flexibility test method, the outer flange 16 may be trimmed as indicated by the cut lines 220. In this manner, as noted above, an injection-molded portion, such as the coupling flange 22 or soft convex insert 26, may be disposed at or near edges of the ostomy appliance 10 for flexibility testing. The ostomy appliance 10 to be tested should be maintained flat during preparation to avoid bending or creasing.

Figure 23:
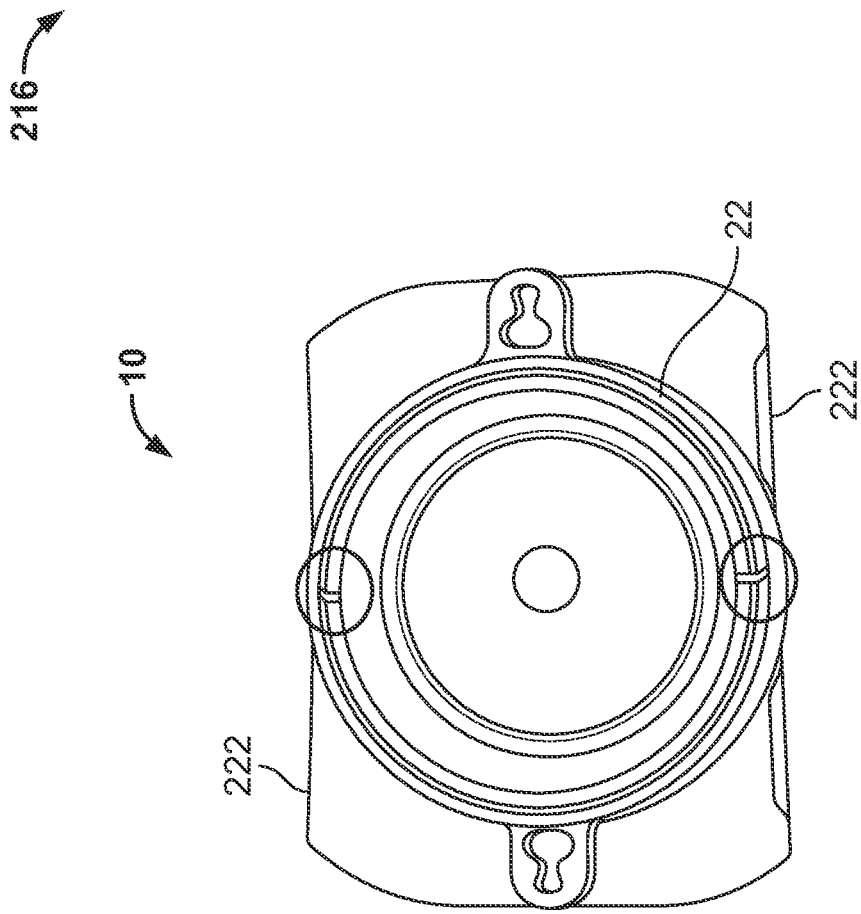
FIG. 23 is a plan view showing an example of a trimmed ostomy appliance for a flexibility test, according to an embodiment.

FIG. 23 is a plan view of the ostomy appliance 10 after trimming for the flexibility test method. As shown in FIG. 23, the cut lines 220, and related trimming, results in two substantially parallel horizontal edges 222, extending tangentially to a 12 o'clock and a 6 o'clock position of the coupling flange 22. If the ostomy appliance for testing is a one-piece product, the ostomy pouch may be removed from the sample for testing as well, for example, by cutting.

Figure 24:
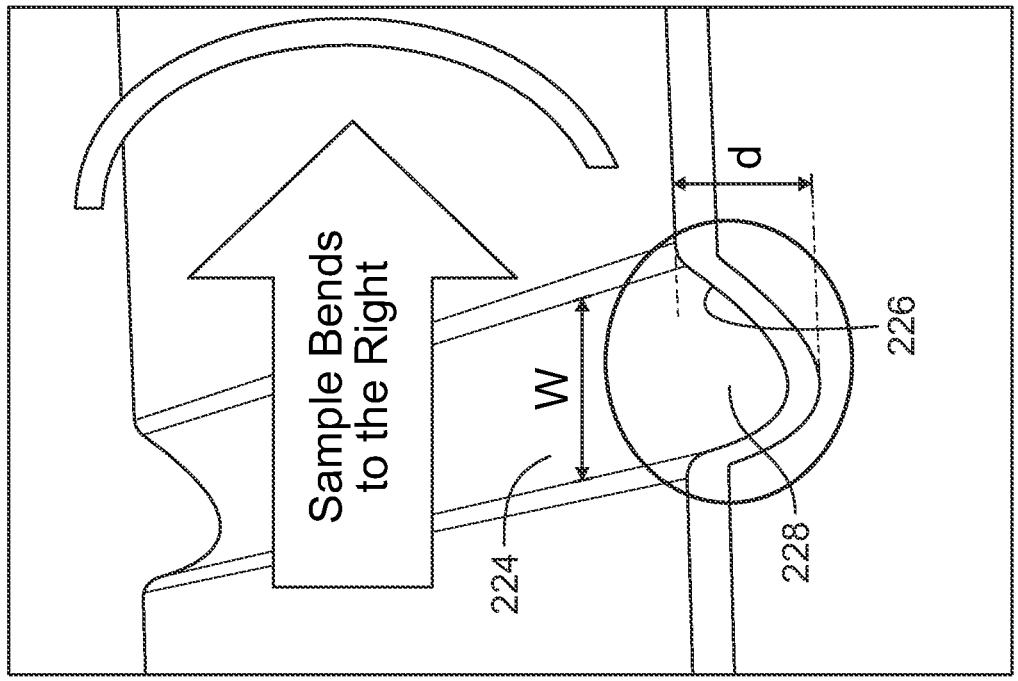
FIG. 24 is an enlarged view of a positioning groove in a tensile testing machine, according to an embodiment.

FIG. 24 is an enlarged view of a positioning groove 224, according to an embodiment. Each of the lower platen insert 216 and the upper platen insert 218 may include the positioning groove 224. The positioning groove 224 may include a first portion 226 having a first length and a second portion 228 having a second length. In one embodiment, the first length may be longer than a second length. In one embodiment the first portion 226 may a first slope and the second portion 228 may have a second slope. An absolute value of the first slope may be less than an absolute value of the second slope. The positioning slot 224 may have a width 'w' and a depth 'd.' A trough (i.e., a point of maximum depth) may be offset from center in the width 'w' direction. The first portion 226 may extend along a surface of the positioning groove 224 from the trough to one end of the positioning groove 224 in the width 'w' direction. The second portion 228 may extend along the surface of the positioning groove 224 from the trough to another, opposite end of the positioning groove 224 in the width 'w' direction. The positioning groove 224 may be sized and shaped to promote bending of the ostomy appliance 10 in a predetermined direction during the flexibility test. For example, the size and shape of the positioning grooves 224 may promote bending of the ostomy appliance to the right in FIG. 24.

FIGS. 25-27 show examples of the ostomy appliance 10 being positioned in the tensile testing machine 210 for the flexibility test. As shown in FIG. 25, the trimmed, horizontal edges 222 may be arranged in respective positioning slots 224 of the upper and lower platen inserts 216, 218. In FIG. 26, a position of the ostomy appliance 10 may be adjusted laterally relative to the upper and lower platen inserts 216, 218 such that a compressive force from the tensile testing machine 210 may applied at a consistent location on different ostomy appliances for different flexibility tests. For example, the ostomy appliance 10 may be substantially centered in a lateral direction of the upper and lower and platen inserts. Referring to FIGS. 26 and 27, the ostomy appliance 10 may include first position markings 230 and second position markings 232. The first and second position markings 230, 232 may be at 0 and 180 degrees (12 o'clock and 6 o'clock), respectively. The upper and lower platen inserts 216,218 may also include third and fourth position markings 234, 236, respectively. The ostomy appliance 10 may be properly positioned relative the upper and the lower platen inserts 216, 218 when the first position marking 230 is substantially aligned with the third position marking 234, and the second position marking 232 is substantially aligned with the fourth position marking 236.

FIG. 28 is a perspective view of the tensile testing machine 210 having an ostomy appliance 10 arranged for the flexibility test, according to an embodiment. As described above, the trimmed horizontal edges 222 of the ostomy appliance 10 may be positioned in the respective positioning grooves 224 of the upper and lower platen inserts 216, 218. In one embodiment, a release liner may be removed from the convex portion 14 of the ostomy appliance and a lint-free wipe may be disposed over the adhesive.

Figure 29:
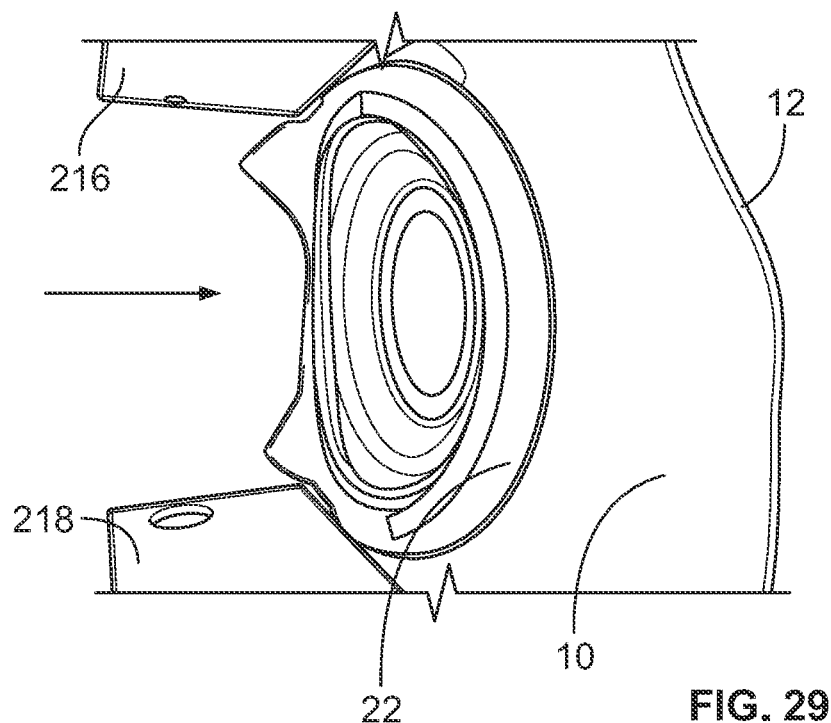
FIG. 29 shows the ostomy appliance in desired bending pattern during a flexibility test, according to an embodiment.

FIG. 29 shows the ostomy appliance 10 in the tensile testing machine 210 during a flexibility test, bending in the desired manner for measuring flexibility, according to an embodiment. As shown in FIG. 29, a desired bending pattern for the ostomy appliance 10 may include the coupling flange 22 bending toward the body-facing side 12 of the ostomy appliance 10 (or, to the right as shown in FIG. 29).

Figure 30:
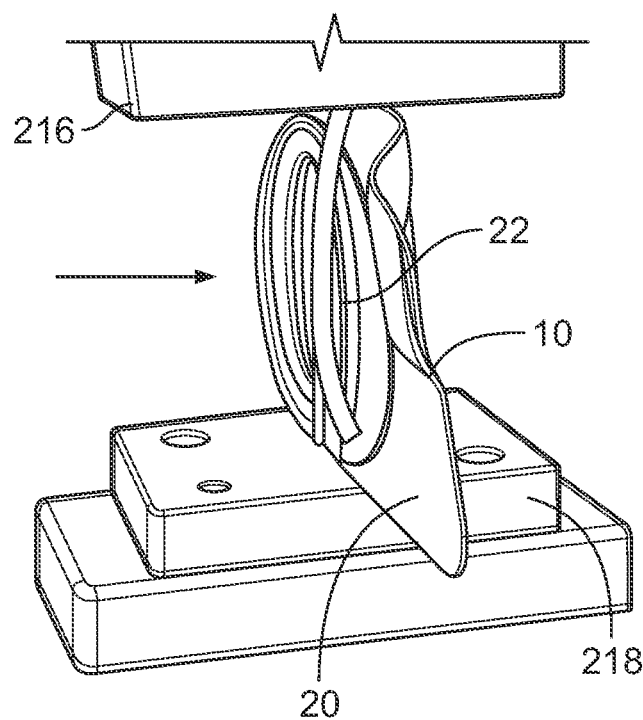
FIG. 30 shows the ostomy appliance in an unintended bending pattern during a flexibility test, according to an embodiment.
Figure 33:
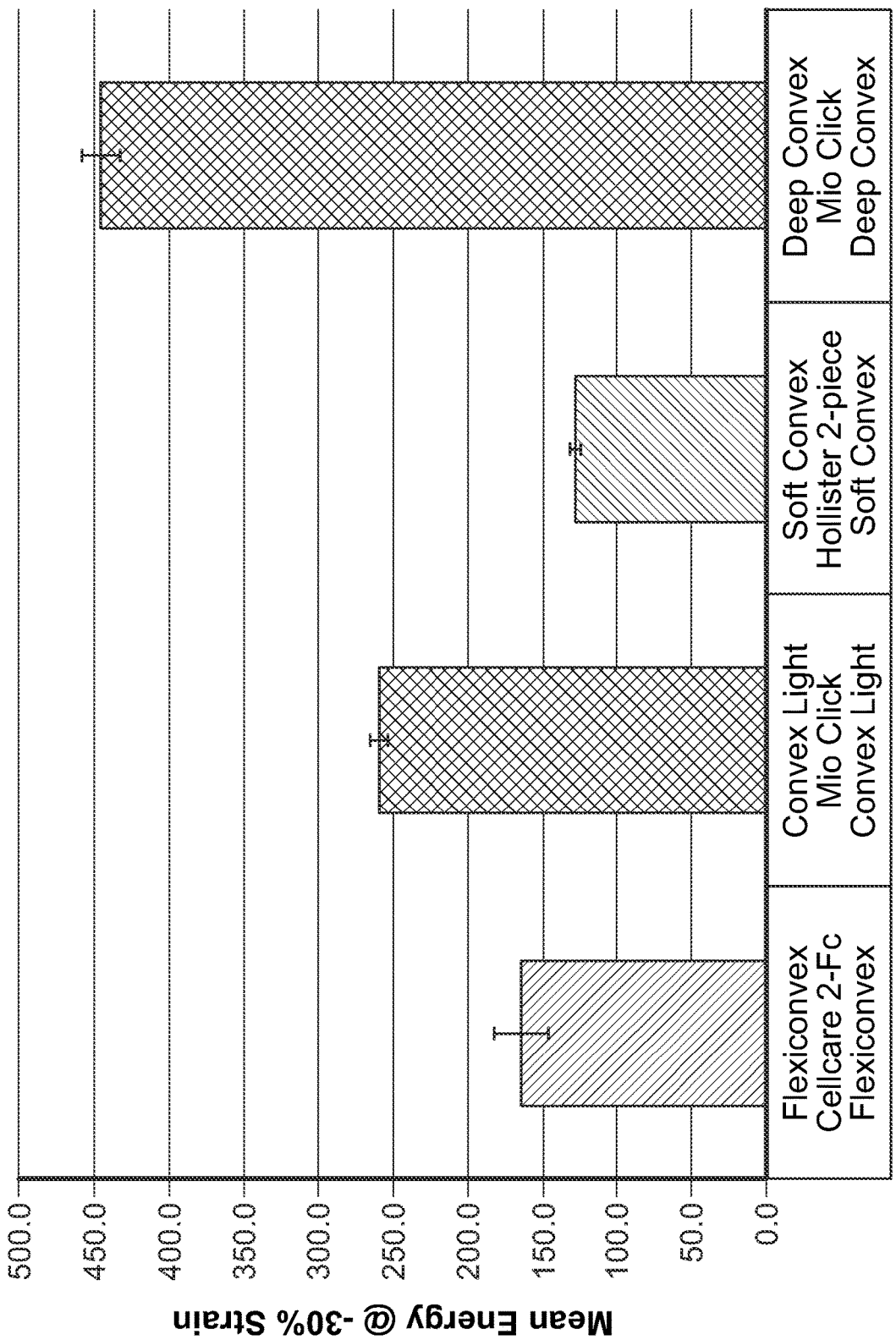
FIG. 33 is a chart showing flexibility test results of different commercial
Figure 34:
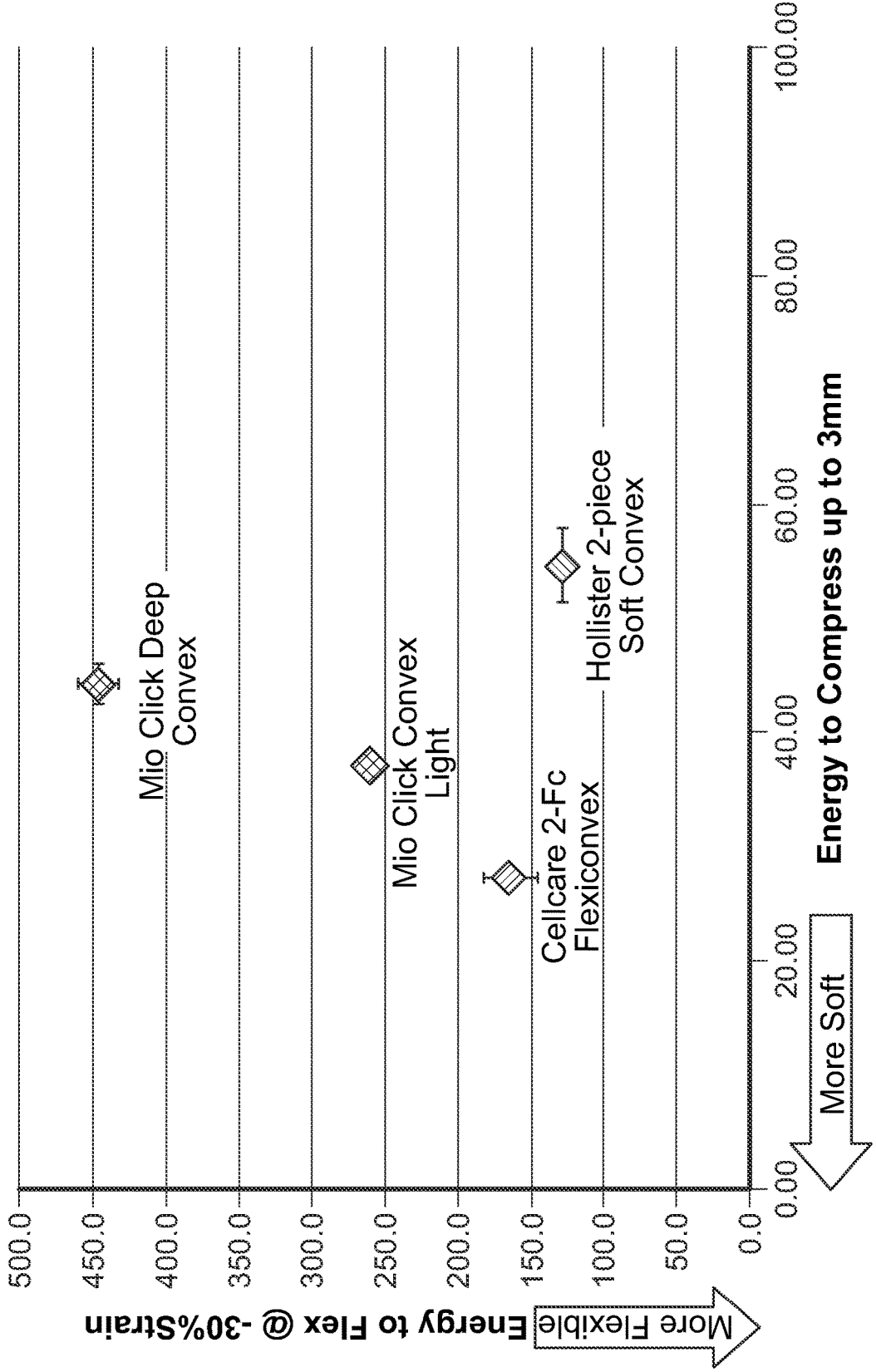
FIG. 34 is a scatterplot showing flexibility and softness test results for different commercial ostomy appliances.
Figure 35:
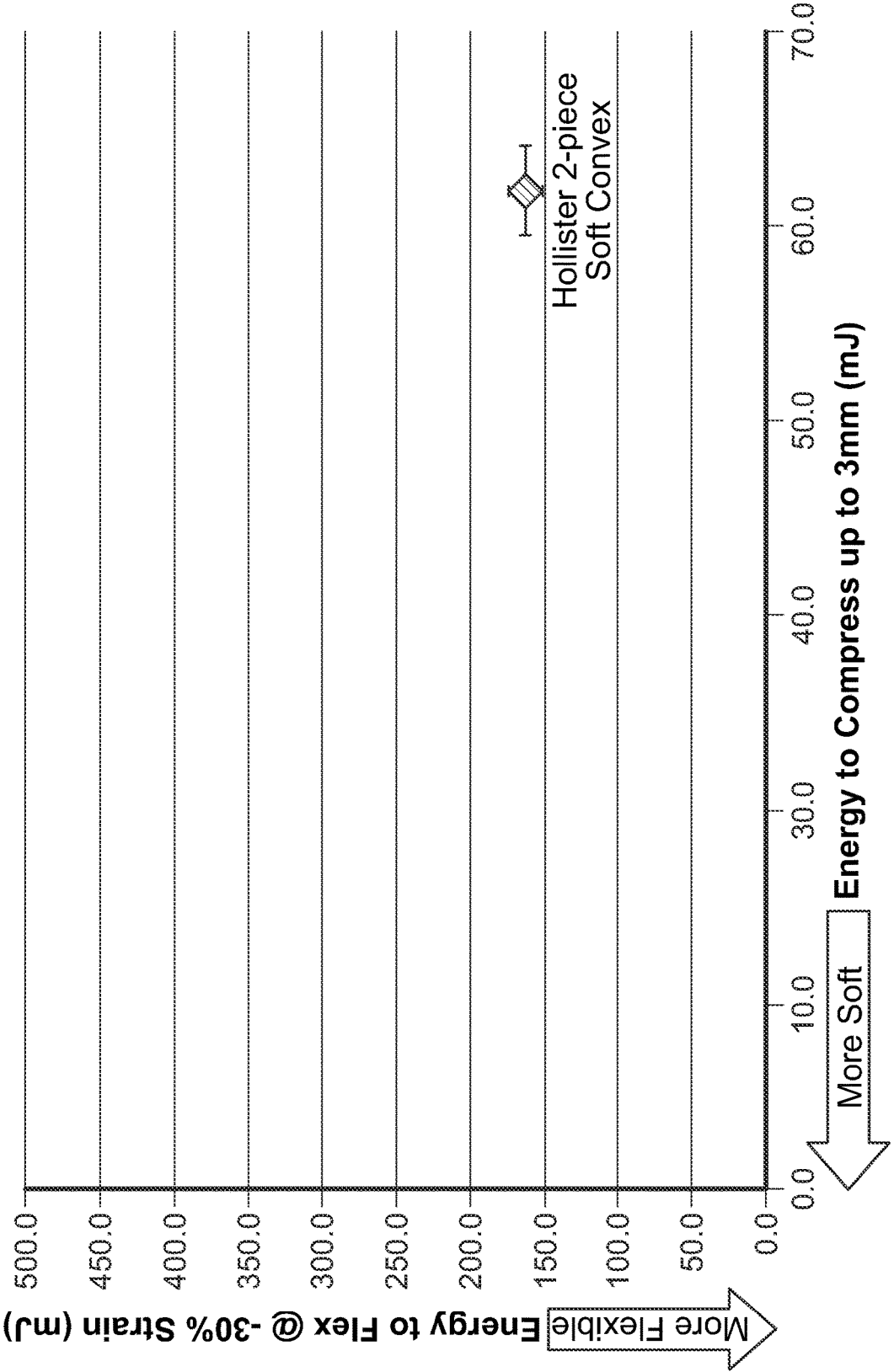
FIG. 35 is a scatterplot showing flexibility and softness test results for a small-sized ostomy appliance according to present embodiments.
Figure 36:
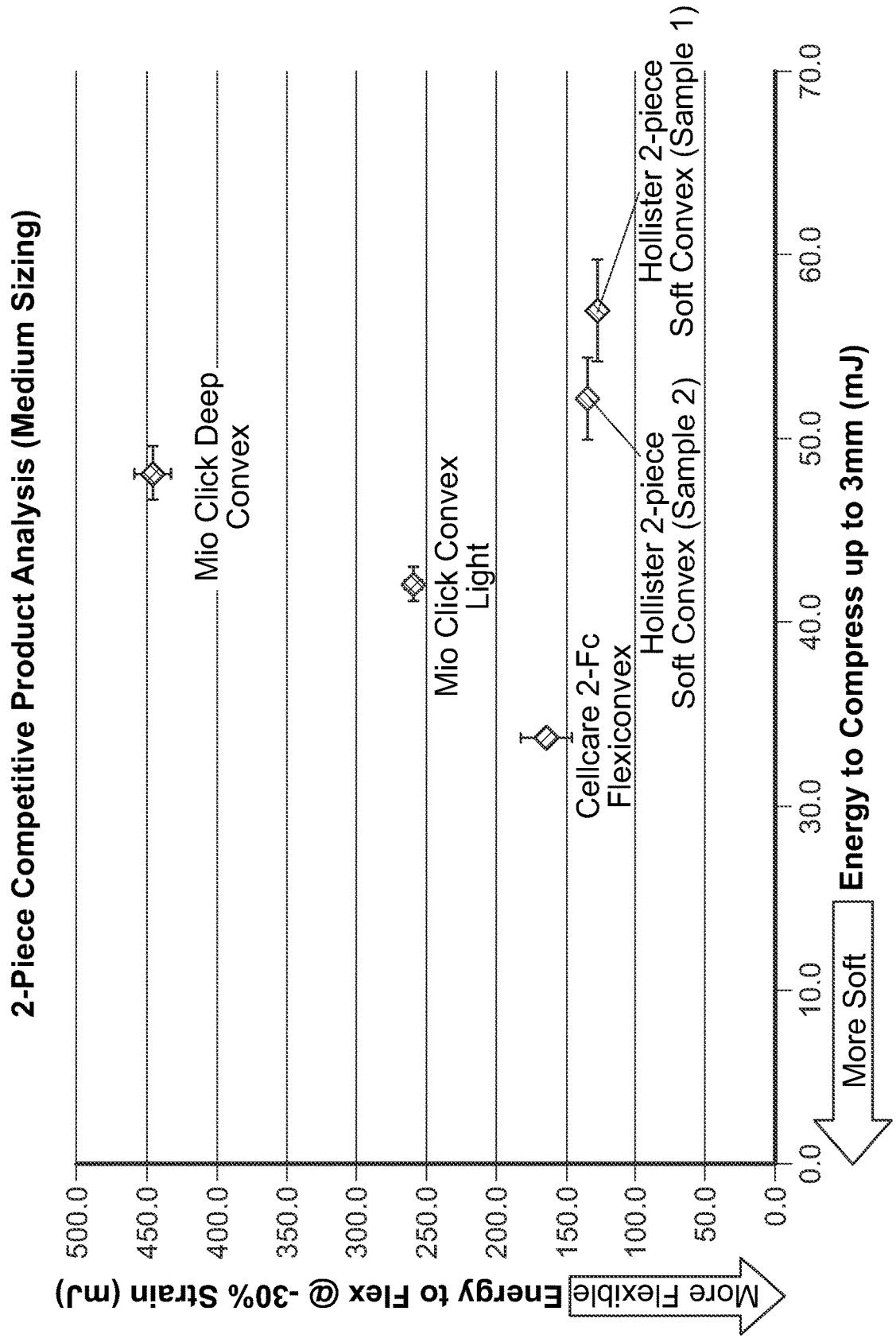
FIG. 36 is a scatterplot showing flexibility and softness test results for different medium-sized commercial ostomy appliances.
Figure 37:
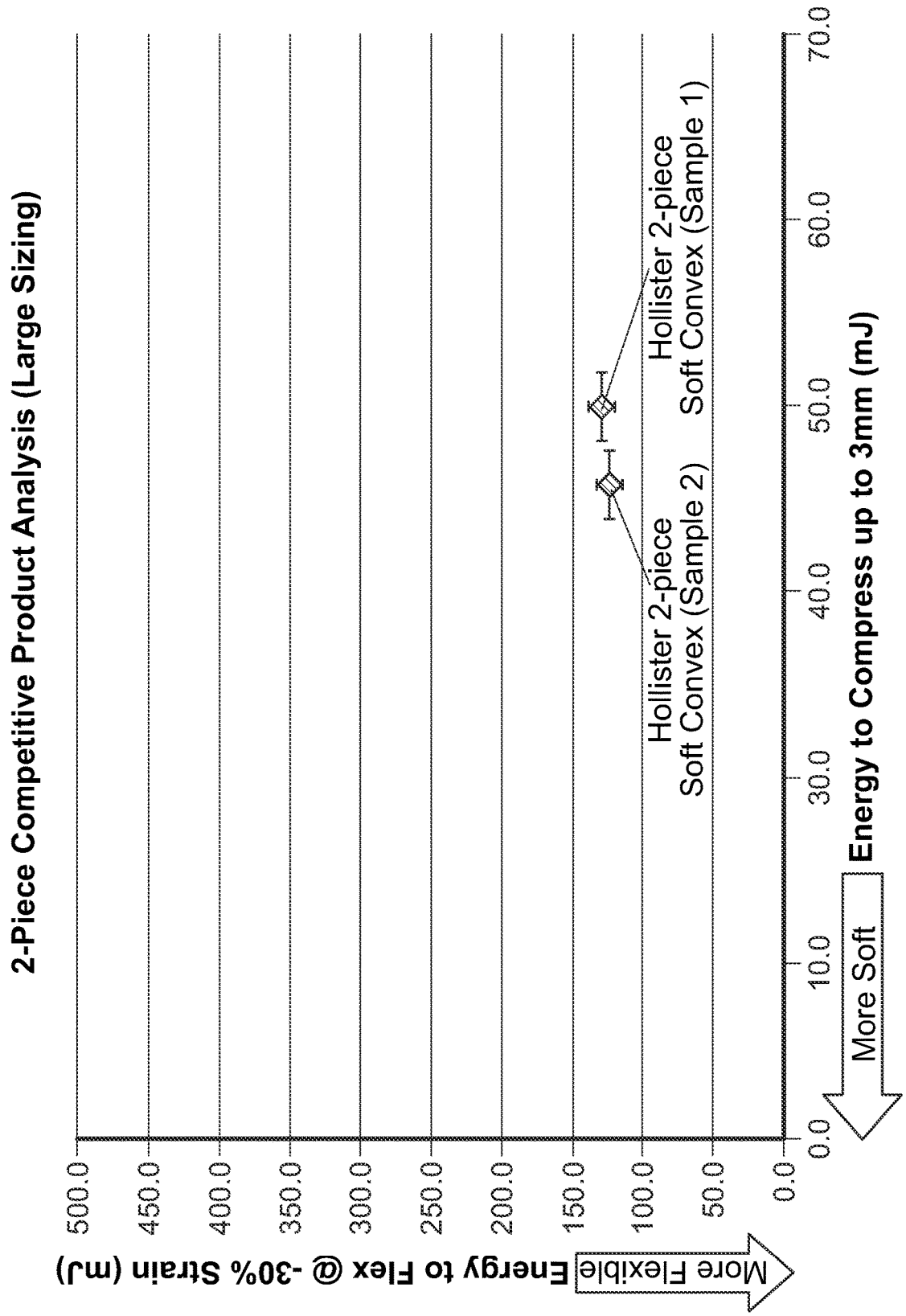
FIG. 37 is a scatterplot showing flexibility and softness test results for large-sized ostomy appliances according to present embodiments.
Figure 38:
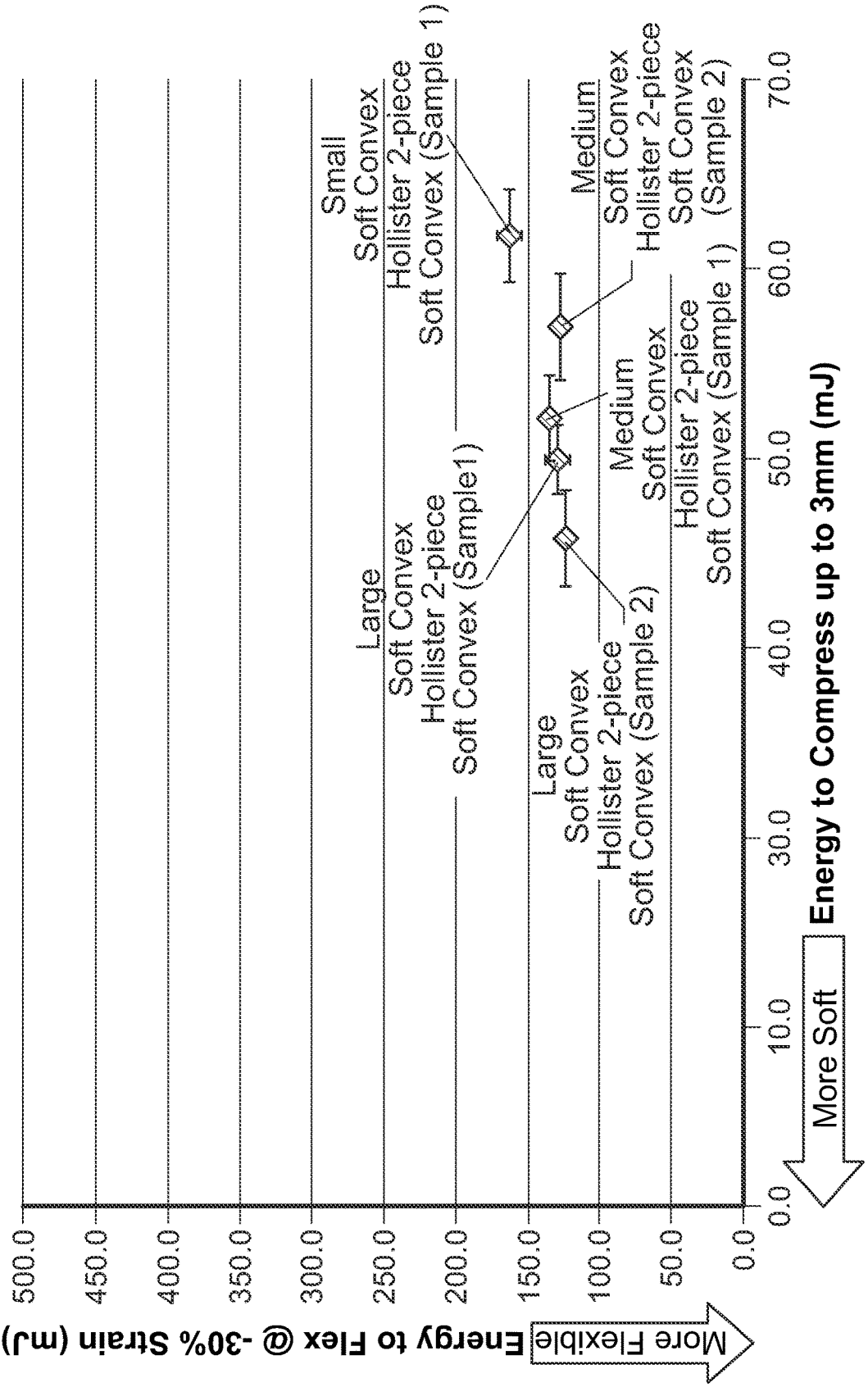
FIG. 38 is a scatterplot showing flexibility and softness test results for differently sized ostomy appliances according to present embodiments.
Figure 39:
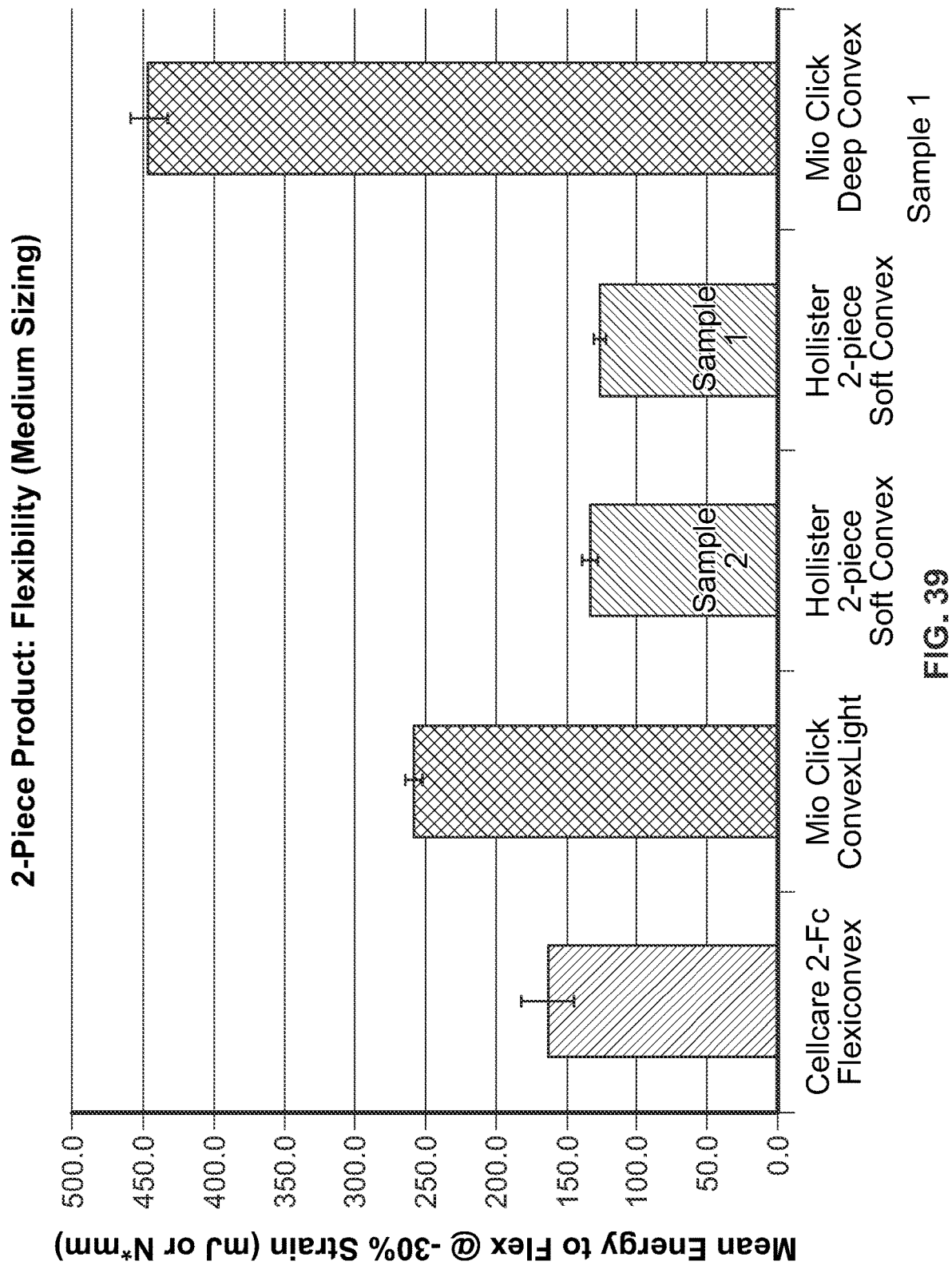
FIG. 39 is a chart showing flexibility test results for different medium-sized commercial ostomy appliances including two ostomy appliances according to present embodiments.
Figure 40:
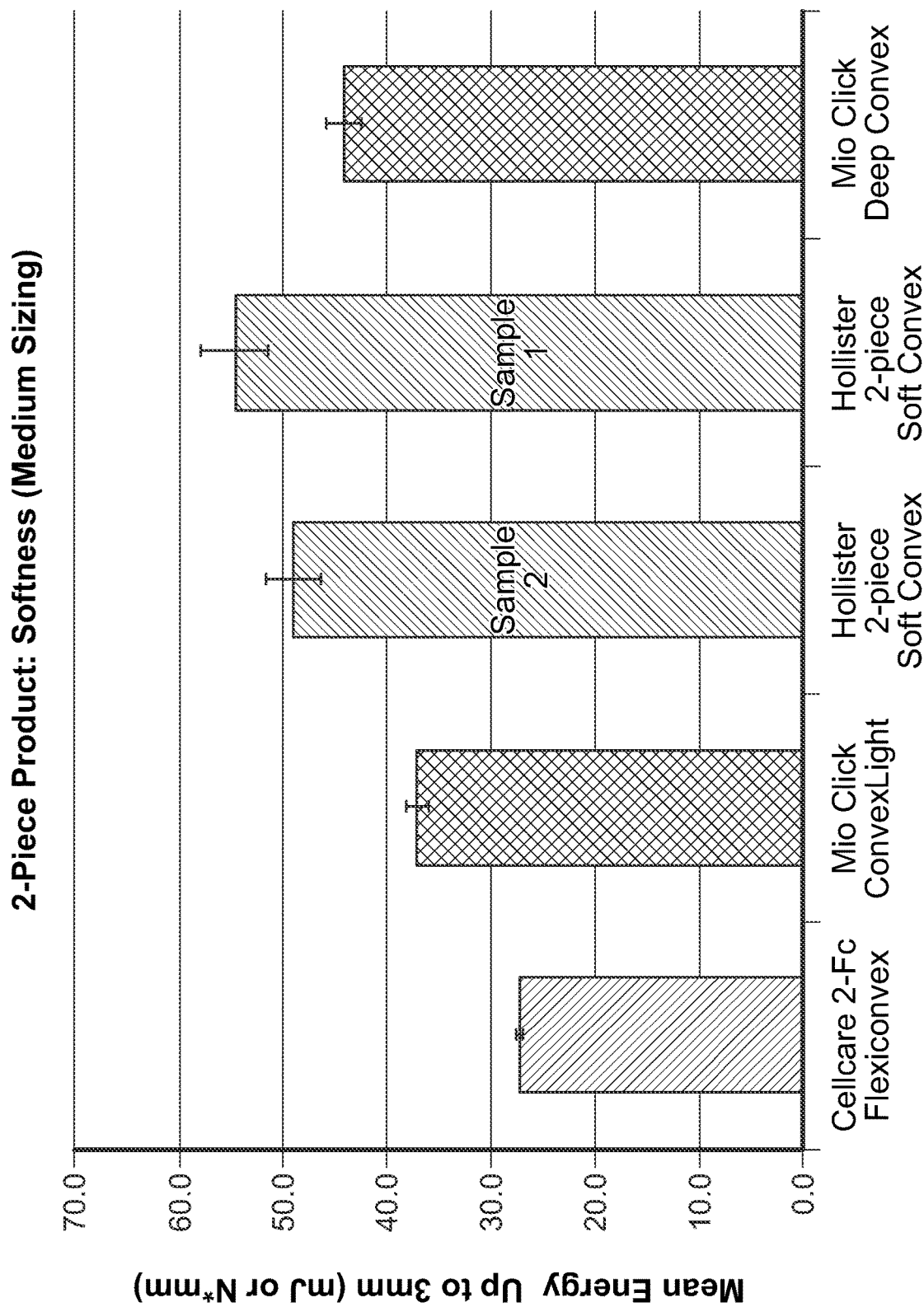
FIG. 40 is a chart showing softness test results for different medium-sized commercial ostomy appliances including two ostomy appliances according to present embodiments.

FIG. 30 shows an example of the ostomy appliance 10 exhibiting an unintended bending pattern during the flexibility test. For example, an unintended bending pattern may include the coupling flange 22 bending toward the pouch-facing side 20 (or, to the left as shown in FIG. 30). In such instances, measurements should not be recorded for determining flexibility of the ostomy appliance 10.

The tensile testing machine 210 may be operated to apply a compressive force to the ostomy appliance 10 arranged between the upper and lower platen inserts 216, 218 as described above, for example, by moving one of the platen inserts toward the other. A diameter or height of a functional part, e.g., the coupling flange 22 and/or soft convex insert 16 may be provided to the tensile testing machine 210. For example, the diameter or height may be provided to a computer having software to control operations of the tensile testing machine 210 to perform the flexibility test. The diameter or height may be measured, for example, with calipers or a ruler, and may refer to the distance between opposite edges of the coupling flange 22 and/or the soft convex insert 16. The diameter or height of each ostomy appliance to be tested may be provided. The computer may be part of the tensile testing machine 210 or a peripheral device operably connected to the tensile testing machine.

Other information regarding the ostomy appliance to be tested may be provided to the tensile testing machine 210 as well. For example, a groove depth and/or flexibility test parameters, such as initial speed, strain end point and data acquisition rate may be provided to the computer. In one embodiment, an initial speed (i.e., a speed of the platen providing the compressive force) may be approximately 10 in/min, the strain end point may be approximately 0.5 in/in and the data acquisition rate may be approximately 10.0 Hz.

In an embodiment, the tensile testing machine 210 may be operated to pre-load to the ostomy appliance 10 to pre-bend the ostomy appliance 10. The pre-bend may be defined in the software controlling the flexibility test and may, for example, have a default value of 2% of the diameter of the functional part of the ostomy appliance 10.

The computer may record and/or calculate various parameters during the flexibility test. Calculations may be performed according to software executed by the computer, for example, software specific to the tensile testing machine 210. Example calculations include a pre-bend force at −2% strain (N) (static force measurement, useful to understand of the ostomy appliance is properly arranged on the upper and lower platen inserts), energy at −30% strain (N*mm) (definite integral from 0 mm extension to 30% of the total functional part diameter or height as a function of load (N); alternatively, may be an "area under the curve" of the force measurement from extension=0 mm to 30% of the total part height (mm)), and/or energy at −X % strain (N*mm) (same as above, but for alternative outputs of the test method if other strain measurements are specified in a testing protocol). The flexibility data may be reported as the "energy at −30% strain" (N*mm) measurement. A minimum of three measurements may be taken per ostomy appliance being tested. The first and second measurements may be discarded, and the third measurement may be reported as the flexibility measurement. In an embodiment, a load cell of the tensile testing machine 210 may be a 50N load cell. The flexibility test may be performed for ostomy appliances of different sizes, such as the small, medium and large sizes described above. The flexibility test may be adapted for other ostomy appliances having sizes different than those described above in an effort to obtain consistent results for reliable flexibility and/or softness comparisons.

The ostomy appliance 10 according to present embodiments was tested for softness and flexibility according to the softness and flexibility test methods described above. Other commercial ostomy appliances were tested according the softness and flexibility test methods described above as well.

FIG. 31 is a table showing softness test results for differently sized ostomy appliances 10 according to embodiments herein and other commercial ostomy appliances, according to the softness test method described above. The ostomy appliance 10 of the present embodiments is labeled as the "Hollister 2-piece Soft Convex" in the "Product" column of FIG. 31. As shown in FIG. 31, the small-sized ostomy appliance 10 according to present embodiments may have a softness in a range of 57.4 N*mm to 63.2 N*mm, based on the mean energy up to 3 mm and the standard deviation. In an embodiment, the small-sized ostomy appliance may have a softness in a range of 54.6 N*mm to 66.0 N*mm. In an embodiment, the small-sized ostomy appliance may have a range of 51.7 N*mm to 68.9 N*mm.

A medium-sized ostomy appliance 10 according to the present embodiments may have a softness in a range of 46.4 N*mm to 51.6 N*mm. In an embodiment, the medium-sized ostomy appliance 10 may have a softness in a range of 43.7 N*mm to 54.2 N*mm. In an embodiment, the medium-sized ostomy appliance 10 may have a softness in a range of 41.1 N*mm to 56.8 N*mm. Another medium-sized ostomy appliance according to present embodiments may have a softness in a range of 51.4 N*mm to 57.9 N*mm. In an embodiment, the medium-sized ostomy appliance 10 may have a softness in a range of 48.1 N*mm to 61.2 N*mm. In an embodiment, the medium-sized ostomy appliance 10 may have a softness in a range of 44.8 N*mm to 64.4 N*mm.

A large-sized ostomy appliance 10 according to present embodiments may have a softness in a range of 38.5 N*mm to 44.5 N*mm. In an embodiment, the large-sized ostomy appliance 10 may have a softness in a range of 35.6 N*mm to 47.4 N*mm. In an embodiment, the large-sized ostomy appliance 10 may have a softness in range of 32.6 N*mm to 50.4 N*mm. Another large-sized ostomy appliance 10 according to present embodiments may have a softness in a range of 44.3 N*mm to 48.5 N*mm. In an embodiment, the large-sized ostomy appliance 10 may have a softness in a range of 42.2 N*mm to 50.6 N*mm. In an embodiment, the large-sized ostomy appliance 10 may have a softness in a range of 40.0 N*mm to 52.8 N*mm.

Thus, ostomy appliances 10 according to the present embodiments generally may have a softness in a range of 32.6.N*mm to 68.9 N*mm. In other embodiments, the ostomy appliances 10 generally may have a softness in a range of about 35.6 N*mm to 66.0 N*mm. In embodiment, the ostomy appliances 10 may have a softness in a range of about 38.5 N*mm to 63.2 N*mm.

FIG. 32 is a table showing flexibility test results for differently sized ostomy appliances 10 according to present embodiments and other commercial ostomy appliances, according to the flexibility test method described above. Energy at −30% strain of each ostomy appliance sample was recorded. The "energy at −30% strain" as used herein is energy expended to deform an ostomy appliance by 30%. Energy expended to deform an object by X % is the work done on the object to deform the object by X %, which is an "area under the curve" of the force measurement (see Eq. 1 below) from extension=0 mm to X % of the total object height (mm):

$$W = \int_0^{X\%} F\,dx \qquad \text{Eq. 1}$$

For the flexibility test, each ostomy appliance sample was prepared and positioned in the tensile testing machine 210 according to the flexibility test method described above. A 50N load cell was used for the tensile testing machine 210. The settings used for the tensile testing machine were: initial speed (i.e., a speed of the platen providing the compressive force) −10 in/min, strain end point −0.5 in/in, and data acquisition rate −10.0 Hz. Compressive force applied to an ostomy appliance sample as the top platen moved down towards the bottom platen was recorded from the initial position of the ostomy appliance sample (X=0) to −30% of the ostomy sample height (X=m). The area under the force measurement curve was calculated to obtain energy at −30% strain of the ostomy appliance sample.

The ostomy appliance 10 of the present embodiments is labeled as the "Hollister 2-piece Soft Convex" in the "Product" column of FIG. 32. As shown in FIG. 32, the small-sized ostomy appliance 10 according to present embodiments may have a flexibility in a range of 155.0 N*mm to 170.8 N*mm, based on the mean energy at −30% strain and the standard deviation. In an embodiment, the small-sized ostomy appliance 10 may have a flexibility in a range of 147.1 N*mm to 178.7 N*mm. In an embodiment, the small-sized ostomy appliance may have a flexibility in a range of 139.2 N*mm to 186.6 N*mm.

A medium-sized ostomy appliance 10 according to the present embodiments may have a flexibility in a range of 129.3 N*mm to 140.1 N*mm. In an embodiment, the medium-sized ostomy appliance 10 may have a flexibility in a range of 123.9 N*mm to 145.5 N*mm. In an embodiment, the medium-sized ostomy appliance 10 may have a flexibility in a range of 118.9 N*mm to 150.9 N*mm. Another medium-sized ostomy appliance according to present embodiments may have a flexibility in a range of 123.8 N*mm to 131.6 N*mm. In an embodiment, the medium-sized ostomy appliance 10 may have a flexibility in a range of 119.9 N*mm to 135.5 N*mm. In an embodiment, the medium-sized ostomy appliance 10 may have a flexibility in a range of 116.0 N*mm to 139.4 N*mm.

A large-sized ostomy appliance 10 according to present embodiments may have a flexibility in a range of 118.7 N*mm to 129.3 N*mm. In an embodiment, the large-sized ostomy appliance 10 may have a flexibility in a range of 113.4 N*mm to 134.4 N*mm. In an embodiment, the large-sized ostomy appliance 10 may have a flexibility in a range of 108.1 N*mm to 139.9 N*mm. Another large-sized ostomy appliance 10 according to present embodiments may have a flexibility in a range of 121.6 N*mm to 138.0 N*mm. In an embodiment, the large-sized ostomy appliance 10 may have a flexibility in a range of 113.4 N*mm to 146.2 N*mm. In an embodiment, the large-sized ostomy appliance 10 may have a flexibility in a range of 105.2 N*mm to 154.4 N*mm.

Thus, ostomy appliances 10 according to the present embodiments generally may have a flexibility in a range of 105.2 N*mm to 186.6 N*mm. In an embodiment, the ostomy appliances 10 generally may have a flexibility in a range of about 113.4 N*mm to 178.7 N*mm. In an embodiment, the ostomy appliances 10 generally may have a flexibility in a range of about 118.7 N*mm to 170.8 N*mm.

In an embodiment, a small-sized ostomy appliance 10 may have a softness in a range of about 51.7 N*mm to 68.9 N*mm and a flexibility in a range of about 139.5 N*mm to 186.6 N*mm. In an embodiment, the small-sized ostomy appliance 10 may have a softness in a range of about 54.6 N*mm to 66.0 N*mm and a flexibility in a range of about 147.1 N*mm to 178.7 N*mm. In an embodiment, the small-sized ostomy appliance 10 may have a softness in a range of about 57.4 N*mm to 63.2 N*mm and a flexibility in a range of about 155 N*mm to 170.8 N*mm.

In an embodiment, a medium-sized ostomy appliance 10 may have a softness in a range of about 41.1 N*mm to 64.4 N*mm and a flexibility in a range of about 116.0 N*mm to 150.9 N*mm. In an embodiment, the medium-sized ostomy appliance 10 may have a softness in a range of about 43.7 N*mm to 61.2 N*mm and a flexibility in a range of about 118.9 N*mm to 145.5 N*mm. In an embodiment, the medium-sized ostomy appliance 10 may have a softness in a range of about 44.8 N*mm to 57.9 N*mm and a flexibility in a range of about 119.9 N*mm to 140.1 N*mm.

In an embodiment, a large-sized ostomy appliance 10 may have a softness in a range of about 32.6 N*mm to 52.8 N*mm and a flexibility in a range of about 105.2 N*mm to 154.4 N*mm. In an embodiment, the large-sized ostomy appliance 10 may have a softness in a range of about 35.6 N*mm to 50.6 N*mm and a flexibility in a range of about 108.1 N*mm to 146.2 N*mm. In an embodiment, the large-sized ostomy appliance 10 may have a softness in a range of about 38.5 N*mm to 50.4 N*mm and a flexibility in a range of about 113.4 N*mm to 139.9 N*mm.

Variations of the present embodiments may provide different softness and/or flexibility characteristics. For example, different geometries for the coupling flange 22 and/or the soft convex insert 26 may vary the softness and/or flexibility characteristics of the ostomy appliance 10. For instance, varying a diameter or thickness of the coupling flange 22 and/or the soft convex insert 26 may vary the softness and/or flexibility characteristics. In addition, or alternatively, selecting different materials for the coupling flange 22 and/or the soft convex insert 26 may vary the softness and/or flexibility characteristics. For example, by forming the coupling flange 22 and/or the soft convex insert 26 from, for example, silicon, thermoplastic elastomer (TPE) or polyurethane (PU) may provide an ostomy appliance 10 having increased softness and/or increased flexibility (i.e., lower energy required to compress or bend the ostomy appliance).

In an embodiment, the ostomy appliance 10 according to present embodiments may have a flexibility less than approximately 145.6 N*mm. In one embodiment, the ostomy appliance 10 may have a flexibility less than approximately 127.3 N*mm. In one embodiment, the ostomy appliance 10 may have a flexibility less than approximately 108.9 N*mm.

In an embodiment, the ostomy appliance 10 according to present embodiments may have a softness less than approximately 63.2 N*mm. In one embodiment, the ostomy appliance 10 may have a softness less than approximately 42.4 N*mm. In an embodiment, the ostomy appliance 10 may have a softness less than approximately 26.2 N*mm.

In one embodiment, the ostomy appliance 10 according to present embodiments may have a softness less than approximately 63.2 N*mm and a flexibility less than approximately 145.6 N*mm, less than approximately 127.3 N*mm or less than approximately 108.9 N*mm.

In an embodiment, the ostomy appliance 10 according to present embodiments may have a softness of at least 27.7 N*mm and less than about 69.5 N*mm, and flexibility less than 253.1 N*mm and greater than about 106.7 N*mm. In an embodiment, the ostomy appliance 10 according to present embodiments may have a softness of at least 30.5 N*mm and less than about 69.5 N*mm, and a flexibility less than 227.8 N*mm and greater than about 106.7 N*mm.

FIGS. 33-40 show various diagrams, including charts and scatterplots showing softness and flexibility test results for the ostomy appliances 10 of the present embodiments and other commercial ostomy appliances, based on the tables shown in FIGS. 31 and 32.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:
    a soft convex insert including;
        a body-side surface;
        a recess; and
        a pouch-side surface, the body-side surface having a convex contour configured to provide a convex portion of the ostomy appliance;
    an adhesive extending over the body-side surface of the soft convex insert;
    a stoma opening configured to receive a stoma;
    a coupling flange connected to the pouch-side surface of the soft convex insert; and
    a floating flange film connecting the coupling flange and the soft convex insert, wherein one end of the floating flange film is attached to the coupling flange and another end of the floating flange film is attached to the soft convex insert within the recess, and
    wherein the ostomy appliance has a softness of about 32.6 N*mm to about 68.9 N*mm, wherein the softness is measured in energy expended to compress 3 mm of the convex portion, and a flexibility of about 105.2 N*mm to about 186.6 N*mm, wherein the flexibility is measured in energy expended to deform the ostomy appliance by 30%.

2. The ostomy appliance of claim 1, wherein the floating flange is configured to allow for movement of the coupling flange relative to the soft convex insert.

3. An ostomy appliance comprising:
    a coupling flange;
    a floating flange film having one end secured to the coupling flange;
    a soft convex insert having a convex contour configured to provide a convex portion of the ostomy appliance and a recess, wherein another end of the floating flange film is secured within the recess;
    an adhesive extending over the soft convex insert; and
    a stoma opening extending through the coupling flange, the floating flange film, and the soft convex insert.

4. The ostomy appliance of claim 3, wherein the ostomy appliance has a softness of about 32.6 N*mm to about 68.9 N*mm, wherein the softness is measured in energy expended to compress 3 mm of the convex portion.

5. The ostomy appliance of claim 1, wherein the ostomy appliance has the softness of about 35.6 N*mm to about 66.0 N*mm.

6. The ostomy appliance of claim 3, wherein the ostomy appliance has a flexibility of about 105.2 N*mm to about 186.6 N*mm, wherein the flexibility is measured in energy expended to deform the ostomy appliance by 30%.

7. The ostomy appliance of claim 1, wherein the ostomy appliance has the flexibility of about 113.4 N*mm to about 178.7 N*mm.

8. The ostomy appliance of claim 1, wherein the ostomy appliance has a softness of about 51.7 N*mm to about 68.9 N*mm, wherein the softness is measured in energy expended to compress 3 mm of the convex portion, and a flexibility of about 139.5 N*mm to about 186.6 N*mm, wherein the flexibility is measured in energy expended to deform the ostomy appliance by 30%.

9. The ostomy appliance of claim 1, wherein the ostomy appliance has a softness of about 54.6 N*mm to about 66.0 N*mm, wherein the softness is measured in energy expended to compress 3 mm of the convex portion, and a flexibility of about 147.1 N*mm to about 178.7 N*mm, wherein the flexibility is measured in energy expended to deform the ostomy appliance by 30%.

10. The ostomy appliance of claim 1, wherein the ostomy appliance has a softness of about 41.1 N*mm to about 64.4 N*mm, wherein the softness is measured in energy expended to compress 3 mm of the convex portion, and a flexibility of about 116.0 N*mm to about 150.9 N*mm, wherein the flexibility is measured in energy expended to deform the ostomy appliance by 30%.

11. The ostomy appliance of claim 1, wherein the ostomy appliance has a softness of about 43.7 N*mm to about 61.2 N*mm, wherein the softness is measured in energy expended to compress 3 mm of the convex portion, and a flexibility of about 118.9 N*mm to about 145.5 N*mm, wherein the flexibility is measured in energy expended to deform the ostomy appliance by 30%.

12. The ostomy appliance of claim 1, wherein the ostomy appliance has a softness of about 32.6 N*mm to about 52.8 N*mm, wherein the softness is measured in energy expended to compress 3 mm of the convex portion, and a flexibility of about 105.2 N*mm to about 154.4 N*mm, wherein the flexibility is measured in energy expended to deform the ostomy appliance by 30%.

13. The ostomy appliance of claim 1, wherein the ostomy appliance has a softness of about 35.6 N*mm to about 50.6 N*mm, wherein the softness is measured in energy expended to compress 3 mm of the convex portion, and a flexibility of about 108.1 N*mm to about 146.2 N*mm, wherein the flexibility is measured in energy expended to deform the ostomy appliance by 30%.

14. The ostomy appliance of claim 1, wherein the ostomy appliance has a softness less than about 63.2 N*mm, wherein the softness is measured in energy expended to compress 3 mm of the convex portion, and a flexibility less than about 145.6 N*mm, wherein the flexibility is measured in energy expended to deform the ostomy appliance by 30%.

15. The ostomy appliance of claim 14, wherein the flexibility is less than about 127.3 N*mm.

16. The ostomy appliance of claim 15, wherein the flexibility is less than about 108.9 N*mm.

17. The ostomy appliance of claim 3, wherein the ostomy appliance has a softness less than about 42.4 N*mm, wherein the softness is measured in energy expended to compress 3 mm of the convex portion, and a flexibility less than about 127.3 N*mm, wherein the flexibility is measured in energy expended to deform the ostomy appliance by 30%.

18. The ostomy appliance of claim 2, wherein the floating flange film includes a base and a corrugated portion, wherein the base extends in an axial direction of the ostomy appliance while the corrugated portion extends radially in an initial condition, wherein the corrugated portion is connected to the coupling flange and the base is connected to the soft convex insert in the recess, wherein the base is configured to axially offset the corrugated portion, wherein the axial offset is accommodated by the recess.

19. The ostomy appliance of claim 3, wherein the floating flange film includes a base and a corrugated portion, wherein the base extends in an axial direction of the ostomy appliance while the corrugated portion extends radially in an initial condition, wherein the corrugated portion is connected to the coupling flange and the base is connected to the soft convex insert in the recess, wherein the base is configured to axially offset the corrugated portion, wherein the axial offset is accommodated by the recess.

* * * * *